United States Patent
Desmet et al.

(10) Patent No.: US 9,701,717 B2
(45) Date of Patent: Jul. 11, 2017

(54) POLYPEPTIDES SPECIFICALLY BINDING TO IL-23

(71) Applicant: COMPLIX NV, Diepenbeek (BE)

(72) Inventors: Johan Desmet, Kortrijk (BE); Maria Paulina Henderikx, Hasselt (BE); Klaartje Somers, Kortessem (BE); Stefan Loverix, Ternat (BE); Mark Vaeck, Hofstade (BE); Ignace Lasters, Antwerp (BE)

(73) Assignee: COMPLIX NV, Diepenbeek (BE)

( * ) Notice: Subject to any disclaimer, the term of this patent is extended or adjusted under 35 U.S.C. 154(b) by 0 days.

(21) Appl. No.: 14/437,069

(22) PCT Filed: Oct. 22, 2013

(86) PCT No.: PCT/EP2013/072031
§ 371 (c)(1),
(2) Date: Apr. 20, 2015

(87) PCT Pub. No.: WO2014/064080
PCT Pub. Date: May 1, 2014

(65) Prior Publication Data
US 2015/0266925 A1 Sep. 24, 2015

Related U.S. Application Data

(60) Provisional application No. 61/716,783, filed on Oct. 22, 2012.

(30) Foreign Application Priority Data

Oct. 22, 2012 (EP) ..................................... 12189485
Jul. 4, 2013 (EP) ..................................... 13175134

(51) Int. Cl.
*C07K 14/00* (2006.01)
*A61K 47/48* (2006.01)
*C07K 16/24* (2006.01)
*A61K 39/00* (2006.01)

(52) U.S. Cl.
CPC ........ *C07K 14/00* (2013.01); *A61K 47/48215* (2013.01); *C07K 16/244* (2013.01); *A61K 2039/505* (2013.01); *C07K 2317/35* (2013.01); *C07K 2317/76* (2013.01); *C07K 2317/92* (2013.01); *C07K 2318/20* (2013.01)

(58) Field of Classification Search
None
See application file for complete search history.

(56) References Cited

FOREIGN PATENT DOCUMENTS

| WO | 2010066740 A1 | 6/2010 |
| WO | 2012092970 A1 | 7/2012 |
| WO | 2012093172 A1 | 7/2012 |
| WO | WO 2013/102659 A2 * | 7/2013 |

OTHER PUBLICATIONS

PCT/EP2013/072031 International Search Report and Written Opinion mailed Feb. 10, 2014, 11 pages.
PCT/EP2013/072031 International Preliminary Report on Patentability mailed Oct. 15, 2014, 14 pages.

* cited by examiner

*Primary Examiner* — Christina Bradley
(74) *Attorney, Agent, or Firm* — Lathrop & Gage LLP; James H. Velema, Esq.

(57) ABSTRACT

The application provides Alphabodies that specifically bind to IL-23, as well as to polypeptides that comprise or essentially consist of such Alphabodies. Also provided herein are nucleic acids encoding such Alphabodies; to methods for preparing such Alphabodies and polypeptides; and in particular to pharmaceutical compositions, that comprise such Alphabodies, polypeptides, nucleic acids and/or host cells.

13 Claims, 7 Drawing Sheets

Figure 5:
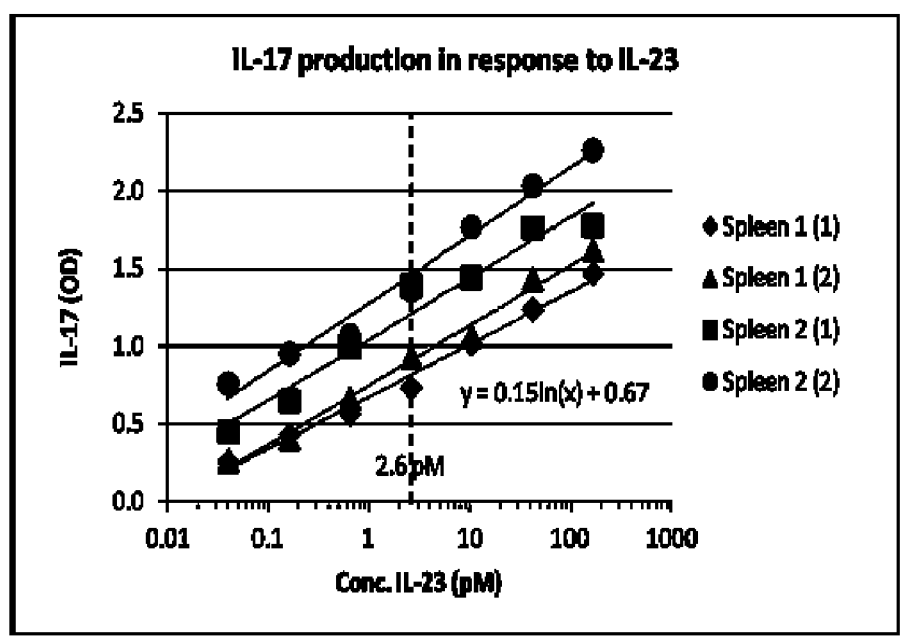

```
 1  MSIEQIQKEITTIQEVIAAIQKYIYTMTGGSG--------------------GSGGMSIEEIQKQIAAIQCQIAAIQKQIYAMTGSGG----------------GGSGMSIEEIQKQIAAIQEQIVAIYKQIMAMAS*
    (SEQ ID NO: 3)
 2  MSIQEIQKEIAQIQAVIAGIQKYIYTMTGGSGSGGGSGGGSGGGSGGSGGMSIEEIQKQIAAIQCQIAAIQKQIYAMTGSGGGGSGGGSGGSGMSIEEIQKQIAAIQEQILAIYKQIMAMVT*
    (SEQ ID NO: 4)
 3  MSIQQIQKEITQIQAVIAGIQKYIYRMTGGSGSGGGSGGGSGGGSGGGSGMSIEEIQKQIAAIQCQIAAIQKQIYAMTGSGG----------------GGSGMSIEEIQKQIAAIQGQIVAIYKQIMAMAI*
    (SEQ ID NO: 5)
 4  MSIKQIQKEIAQIQEVIAAIQKWIYRMTGGSG--------------------GSGGMSIEEIQKQIAAIQCQIAAIQKQIYAMTGSGGGGSGGGSGGSGMSIEEIQKQIAAIQDQIVAIYKQIMAMSS*
    (SEQ ID NO: 6)
 5  MSIQEIQKEIANIQAVIAGIQKYIYTMTGGSGSGGGSGGGSGGMSIEEIQKQIAAIQCQIAAIQKQIYAMTGSGG----------------GGSGMSIEEIQKQITAIQAQIIAIYKQIMAMPR*
    (SEQ ID NO: 7)
 6  MSIQQIQKEITNIQEVIAAIQKWIYTMTGGSG--------------------GSGGMSIEEIQKQIAAIQCQIAAIQKQIYAMTGSGGGGSGGGSGGSGMSIEEIQKQIAAIQNQILAIYKQIMAMGS*
    (SEQ ID NO: 8)
 7  MSIQQIQKEITTIQAVIAAIQKWIYTMTGGSGSGGGSGGGSGGGSGGSGGMSIEEIQKQIAAIQGQIIAIYKQIMAMKD*
    (SEQ ID NO: 9)
 8  MSIQEIQKEIKQIQEVIAGIQKYIYGMTGGSG--------------------GSGGMSIEEIQKQIAAIQCQIAAIQKQIYAMTGSGG----------------GGSGMSIEEIQKQIAAIQNQILAIYKQIMAMPQ*
    (SEQ ID NO: 10)
 9  MSIQQIQKEIATIQEVIAGIQKYIYRMTGGSGSGGGSGGGSGGGSGMSIEEIQKQIAAIQCQIAAIQKQIYAMTGSGG----------------GGSGMSIEEIQKQIAAIQGQILAIYKQIMAMAI*
    (SEQ ID NO: 11)
10  MSIQKIQKEITNIQEVIAAIQKYIYTMTGGSG--------------------GSGGMSIEEIQKQIAAIQCQIAAIQKQIYAMTGSGGGGSGGGSGGSGMSIEEIQKQIAAIQRQILAIYKQIMAMST*
    (SEQ ID NO: 12)
11  MSIEQIQTEIASIQEVIAGIQKYIYSMTGGSG--------------------GSGGMSIEEIQKQIAAIQCQIAAIQKQIYAMTGSGG----------------GGSGMSIEEIQKQIAAIQNQIVAIYKQIMAMGG*
    (SEQ ID NO: 13)
12  MSIQQIQKEIANIQEVIAAIQKWIYLMTGGSG--------------------GSGGMSIEEIQKQIAAIQCQIAAIQKQIYAMTGSGG----------------GGSGMSIEEIQKQIAAIQEQIVAIYKQIMAMPS*
    (SEQ ID NO: 14)
13  MSIEEIQKEIKNIQEVIAAIQKYIYTMTGGSG--------------------GSGGMSIEEIQKQIAAIQCQIAAIQKQIYAMTGSGGGGSGGGSGGSGMSIEEIPKQIAAIQDQIIAIYKQIMAMTR*
    (SEQ ID NO: 15)
14  MSIQQIQKEITQIQEVIAAIQKYIYRMTGGSG--------------------GSDGMSIEEIQKQIAAIQCQIAAIQKQIYAMTGSGG----------------GGSGMSIEEIQKQIAAIQGQILAIYKQIMAMSL*
    (SEQ ID NO: 16)
15  MSIQQIQKEIAQIQEVIAAIQKWIYSMTGGSG--------------------GSGGMSIEEIQKQIAAIQCQIAAIQKQIYAMTGSGG----------------GGSGMSIEEIQKQIAAIQDQIVAIYKQIMAMSG
    (SEQ ID NO: 17)
16  MSIQQIQKEIKQIQEVIAGIQKYIYRMTGGSG--------------------GSGGMSIEEIQKQIAAIQCQIAAIQKQIYAMTGSGG----------------GGSGMSIEEIQKQIAAIQDQILAIYKQIMAMAQ
    (SEQ ID NO: 18)
17  MSIEEIQKQIASIQEVIAGIQKWIYMMTGGSG--------------------GSGGMSIEEIQKQIAAIQKQIAAIQKQIYAMTGSGG----------------GSGMSIEEIQKQITAIKEQIIAIYKQIMAMTP
    (SEQ ID NO: 19)
18  MSIQQIQKEIAQIQEVIAGIQKWIYMMTGGSGSGGGSGGGSGGGSGGGSGMSIEEIQKQIAAIQCQIAAIQKQIYAMTGSGGGGSGGGSGGSGMSIEEIQKQITAIKEQIIAIYKQIMAMTP
    (SEQ ID NO: 20)
19  MSIQQIQKEIAQIQEVIAGIQKWIYMMTGGSGSGGGSGGGSGGGSGGGSGMSIEEIQKQIAAIQCQIAAIQKQIYAMTGSGGGGSGGGSGGSGMSIEEIQKQITAIQEQIIAIYKQIMAMTP
    (SEQ ID NO: 21)
20  MSIQQIQKEIAQIQEVIAAIQKWIYSMTGGSGSGGGSGGGSGGGSGGGSGMSIEEIQKQIAAIQCQIAAIQKQIYAMTGSGGGGSGGGSGGSGMSIEEIQKQITAIQEQIIAIYKQIMAMTP
    (SEQ ID NO: 22)
```

Figure 1

|   |              | A-helix                          | Linkers & B-helix | C-helix                      |
|---|--------------|----------------------------------|-------------------|------------------------------|
| # | Polypeptide  | 1b 1c 1f 1g 2b 2c 2f 2g 3c 3g 4c | L1  Bhel  L2      | 2b 2e 2f 3b 3e 4b 4e 4f      |
| 1 | MB23         | E Q K E T T E V A Y T            | L8  B2fC  L8      | A Q E V Y M A S              |
| 2 | MA12         | Q E K E A Q A V G Y T            | L16 B2fC L16      | A Q E L Y M V T              |
| 3 | MB64         | Q Q K E T Q A V G Y R            | L16 B2fC L8       | A Q G V Y M A T              |
| 4 | MA5          | K Q K E A Q E V A W R            | L8  B2fC L16      | A Q D V Y M S S              |
| 5 | MA15         | Q E K E A N A V G Y T            | L16 B2fC L8       | T Q A I Y M P R              |
| 6 | MB9          | Q Q K E T N E V A W T            | L8  B2fC L16      | A Q N L Y M G S              |
| 7 | MA9          | Q Q K E T T A V A W T            | L16 B2fC L8       | A Q G I Y M K D              |
| 8 | MB38         | Q E K E K Q E V G Y G            | L8  B2fC L8       | A Q N L Y M P Q              |
| 9 | MB74         | Q Q K E A T E V G Y R            | L16 B2fC L8       | A Q G L Y M A I              |
| 10 | MB67        | Q K K E T N E V A Y T            | L8  B2fC L16      | A Q R L Y M S T              |
| 11 | MA14        | E Q T E A S E V G Y S            | L8  B2fC L8       | A Q N V Y M G G              |
| 12 | MA23        | Q Q K E A N E V A W L            | L8  B2fC L8       | A Q E V Y M P S              |
| 13 | MB43        | E E K E K N E V A Y T            | L8  B2fC L16      | A Q D I Y M T R              |
| 14 | MB76        | Q Q K E T Q E V A Y R            | L8  B2fC L8       | A Q G L Y M S L              |
| 15 | MAcons      | Q Q K E A Q E V A W S            | L16 B2fC L8       | A Q D V Y M S G              |
| 16 | MBcons      | Q Q K E K Q E V A Y R            | L8  B2fC L8       | A Q D L Y M A Q              |
| 17 | Cl59        | E E K Q A S E V G W M            | L16  -   L16      | T K E I Y M T P              |
| 18 | Cl59m       | Q Q K E A Q E V G W M            | L16  -   L16      | T K E I Y M T P              |
| 19 | 59m_C2eQ    | Q Q K E A Q E V G W M            | L16 B2fC L16      | T Q E I Y M T P              |
| 20 | 59m_A3cA_A4cS_C2eQ | Q Q K E A Q E V A W S     | L16 B2fC L16      | T Q E I Y M T P              |

Figure 2

| # | Polypeptide | Eq. ELI. KD (nM) | Kin. ELI. k_on ($M^{-1}s^{-1}$) | Kin. ELI. k_off ($s^{-1}$) | Kin. ELI. KD (nM) | Ph.coat KD (nM) |
|---|---|---|---|---|---|---|
| 1 | MB23 | 0.17 | 1.5E+06 | 2.1E-04 | 0.15 | 0.07 |
| 2 | MA12 | 0.11 | 8.1E+05 | 2.1E-04 | 0.26 | 0.08 |
| 3 | MB64 | 0.21 | 1.1E+06 | 3.3E-04 | 0.30 | 0.09 |
| 4 | MA5 | 0.10 | 4.5E+06 | 1.6E-04 | 0.03 | 0.2 |
| 5 | MA15 | 0.31 | 8.0E+05 | 7.2E-05 | 0.09 | 0.12 |
| 6 | MB9 | 0.27 | 1.9E+06 | 2.5E-04 | 0.13 | 0.2 |
| 7 | MA9 | 0.17 | 1.4E+06 | 3.5E-04 | 0.25 | 0.2 |
| 8 | MB38 | 0.20 | 1.0E+06 | 2.2E-04 | 0.21 | 0.18 |
| 9 | MB74 | 0.35 | 6.5E+05 | 1.6E-04 | 0.25 | 0.47 |
| 10 | MB67 | 0.25 | 1.6E+06 | 2.2E-04 | 0.14 | 0.21 |
| 11 | MA14 | 1.8 | 2.0E+05 | 5.0E-04 | 2.5 | 1.5 |
| 12 | MA23 | 0.29 | 4.5E+05 | 3.2E-04 | 0.70 | 0.7 |
| 13 | MB43 | 0.20 | 1.3E+06 | 1.4E-04 | 0.11 | 0.18 |
| 14 | MB76 | 1.83 | 2.5E+05 | 5.6E-04 | 2.3 | 0.16 |
| 15 | MAcons | 0.23 | 2.5E+06 | 3.2E-04 | 0.13 | ND |
| 16 | MBcons | 2.8 | 2.2E+05 | 5.9E-04 | 2.7 | ND |
| 17 | Cl59 | 3.8 | 1.0E+05 | 7.0E-04 | 7.0 | 3.0 |
| 18 | Cl59m | ND | ND | ND | ND | ND |
| 19 | 59m_C2eQ | 0.93 | 1.1E+05 | 4.3E-04 | 3.9 | ND |
| 20 | 59m_A3cA_A4cS_C2eQ | 0.39 | 3.5E+05 | 2.6E-04 | 0.75 | ND |

Figure 3

| # | Polypeptide | Spleno fKD (nM) | Spleno n data (-) | DB fKD (nM) | DB n data (-) |
|---|---|---|---|---|---|
| 1 | MB23 | 0.20 | 4 | 0.16 | 2 |
| 2 | MA12 | 0.13 | 5 | 0.35 | 2 |
| 3 | MB64 | 0.18 | 5 | 0.46 | 2 |
| 4 | MA5 | 1.15 | 3 | 0.45 | 2 |
| 5 | MA15 | 0.48 | 3 | 0.29 | 2 |
| 6 | MB9 | 0.36 | 4 | 0.70 | 2 |
| 7 | MA9 | 0.46 | 3 | 0.24 | 2 |
| 8 | MB38 | 1.01 | 3 | 0.66 | 1 |
| 9 | MB74 | 0.90 | 1 | 1.80 | 1 |
| 10 | MB67 | 1.33 | 2 | ND | 0 |
| 11 | MA14 | 11.00 | 1 | ND | 0 |
| 12 | MA23 | 10.00 | 1 | ND | 0 |
| 13 | MB43 | 0.88 | 2 | ND | 0 |
| 14 | MB76 | 1.70 | 1 | ND | 0 |
| 15 | MAcons | 4.10 | 1 | ND | 0 |
| 16 | MBcons | 0.65 | 1 | 0.80 | 1 |
| 17 | Cl59 | 68.75 | 3 | ND | 0 |
| 18 | Cl59m | 21.69 | 5 | 1.73 | 2 |
| 19 | 59m_C2eQ | 1.90 | 1 | ND | 0 |
| 20 | 59m_A3cA_A4cS_C2eQ | 0.70 | 1 | ND | 0 |

Figure 4

POLYPEPTIDES SPECIFICALLY BINDING TO IL-23

RELATED APPLICATIONS

This application is a 35 U.S.C. §371 filing of International Application No. PCT/EP2013/072031, filed Oct. 22, 2013, which claims priority to U.S. Patent Application No. 61/716,783 filed Oct. 22, 2012, European Patent Application No. 12189485.1, filed Oct. 22, 2012, and European Patent Application No. 13175134.9, filed Jul. 4, 2013, each of which is incorporated herein by reference in its entirety.

FIELD OF THE INVENTION

The application relates to binding agents directed against interleukin-23 (IL-23) as well as uses thereof for prophylactic, therapeutic or diagnostic purposes and in screening and detection.

BACKGROUND

A well characterized family of cytokines is the superfamily of heterodimeric cytokines including IL-12, IL-23, IL-27, CLC-sCNTFR, CLC-CLF-1 and IL-35, all of which bind heterodimeric receptors. Heterodimeric cytokines consist of two different subunits. One of these subunits comprises a four-helix bundle domain. IL-23 consists of the p40 subunit, which is shared with the cytokine IL-12, and the p19 or IL-23 alpha subunit which has a 4-helix bundle structure. IL-23 plays an important role in the inflammatory response against infection. It promotes up-regulation of the matrix metalloprotease MMP9, increases angiogenesis and reduces CD8+ T-cell infiltration. Recently, IL-23 has been implicated in the development of cancerous tumors. In conjunction with IL-6 and TGF-β1, IL-23 stimulates naive CD4+ T cells to differentiate into a novel subset of cells called Th17 cells, which are distinct from the classical Th1 and Th2 cells. Th17 cells produce IL-17, a pro-inflammatory cytokine that enhances T cell priming and stimulates the production of pro-inflammatory molecules such as IL-1, IL-6, TNF-alpha, NOS-2, and chemokines resulting in inflammation.

It has been shown that IL-23 is an important mediator of organ specific autoimmune diseases (Yen et al., 2006). Knockout mice deficient in either p40 or p19, or in either subunit of the IL-23 receptor (IL-23R and IL12R-β1) develop less severe symptoms of multiple sclerosis and inflammatory bowel disease. In addition, it has been demonstrated that anti-IL-23(p19) specific antibodies can inhibit EAE, a preclinical animal model of human MS (Chen et al., 2006).

The therapeutic antibodies Ustekinumab (previously also known under the experimental name ONTO 1275 and now approved for the treatment of plaque psoriasis) and Briakinumab (in phase III clinical trial for the treatment of plaque psoriasis and in phase II trial for MS) are human monoclonal antibodies that neutralize both IL-12 as well as IL-23. There is a concern about adverse effects, more in particular the risk for infections, resulting from the IL23/IL-12 cross-reactivity. While Lima et al. (2009) indicated that no cases of tuberculosis or other opportunistic infections were reported in clinical studies using Ustekinumab, the medication guide for STELARA™ states that 'Some people have serious infections while taking STELARA™, including tuberculosis (TB), and infections caused by bacteria, fungi, or viruses. Some people have to be hospitalized for treatment of their infection'. In addition, the side effects reported for Ustekinumab at the Drug.com web site (Drug Information Online) show up to 5% upper respiratory tract infections.

WO2010/066740 describes Alphabody scaffolds as single-chain triple-stranded alpha-helical coiled coil scaffolds. In addition, WO2012/093172 describes Alphabodies directed against cytokines and growth factors, including IL-23.

SUMMARY OF THE INVENTION

Disclosed herein are improved binding agents to interleukin-23 (IL-23). It has been found that using the Alphabody scaffold, binders can be generated, which bind to IL-23 with high affinity and specificity and which moreover are capable of neutralizing IL-23 activity. More particularly, an Alphabody motif has been identified which confers these properties onto an Alphabody polypeptide. Such binders have several advantages over the traditional (immunoglobulin and non-immunoglobulin) binding agents known in the art. Advantages include, without limitation, the fact that they are compact and small in size (between 10 and 14 kDa, which is 10 times smaller than an antibody), they are extremely stable (having a melting temperature of more than 100° C.) and that they can be made resistant to different proteases. Moreover it was shown that the present binders have reduced immunogenicity in humans compared to commercial IL-23 antibodies.

Provided herein are polypeptides comprising an amino acid sequence that specifically binds to IL-23 and uses of such polypeptides for prophylactic, therapeutic or diagnostic purposes. More particularly the polypeptides envisaged herein comprise one or more Alphabodies directed against IL-23, which are characterized by a sequence motif which ensures improved properties over known IL-23 binders and known Alphabodies directed against IL-23. Indeed it has been found that the presence of a particular sequence motif ensures improved properties such as the ability to effectively neutralize the biological activity of IL-23.

In one aspect, polypeptides are provided specifically binding to IL-23 comprising an amino acid sequence having the general formula HRS1-L1-HRS2-L2-HRS3, and characterized by the features of an Alphabody. More particularly, the amino acid sequence having the general formula HRS1-L1-HRS2-L2-HRS3 is characterized in that:

each of HRS1, HRS2 and HRS3 independently comprise a heptad repeat sequence (HRS) comprising or consisting of 2 to 7 consecutive but not necessarily identical heptad repeat units, the heptad repeat units are 7-residue (poly)peptide represented as 'abcdefg' or 'defgabc', wherein the symbols 'a' to 'g' denote conventional heptad positions, at least 50% of all heptad a- and d-positions are occupied by isoleucine residues, each HRS starts with an aliphatic or aromatic amino acid residue located at a heptad a-position or 'd" position, each of L1 and L2 are independently a linker fragment, which covalently connect HRS1 to HRS2 and HRS2 to HRS3, respectively.

The polypeptides envisaged herein are further characterized in that the HRS1 and HRS3 of the HRS1-L1-HRS2-L2-HRS3 motif further comprise a specific sequence motif. More particularly, the amino acid sequences envisaged herein are characterized in that:

in HRS1:
(i) the heptad f-position of the second heptad repeat unit is occupied by glutamic acid or alanine, (ii) the heptad g-position of the second heptad repeat unit is occupied by valine,
(iii) the heptad c-position of the third heptad repeat unit is occupied by alanine or glycine, and
(iv) the heptad g-position of the third heptad repeat unit is occupied by tyrosine or tryptophan, and
in HRS3:
(i) the heptad e-position of the second heptad repeat unit is occupied by glutamine or lysine,
(ii) the heptad b-position of the third heptad repeat unit is occupied by leucine or isoleucine or valine,
(iii) the heptad e-position of the third heptad repeat unit is occupied by tyrosine, and
(iv) HRS3 comprises a partial (a-f) heptad repeat unit following the third heptad repeat and the heptad b-position therein is occupied by methionine.

In particular embodiments, the polypeptides envisaged herein are characterized in that in HRS1:
(i) the heptad f-position of the second heptad repeat unit is occupied by glutamic acid, and/or
(ii) the heptad g-position of the second heptad repeat unit is occupied by valine, and/or
(iii) the heptad c-position of the third heptad repeat unit is occupied by alanine, and/or
(iv) the heptad g-position of the third heptad repeat unit is occupied by tyrosine In further particular embodiments, the polypeptide envisaged herein are characterized in that in HRS3:
(i) the heptad e-position of the second heptad repeat unit is occupied by glutamine, and/or
(ii) the heptad b-position of the third heptad repeat unit is occupied by valine, and/or
(iii) the heptad e-position of the third heptad repeat unit is occupied by tyrosine, and/or
(iv) HRS3 comprises a partial (a-f) heptad repeat unit following the third heptad repeat and the heptad b-position therein is occupied by methionine.

In further particular embodiments, the polypeptides envisaged herein are characterized in that in HRS1:
(i) the heptad b-position of the first heptad repeat unit is occupied by glutamic acid, and/or
(ii) the heptad c-position of the first heptad repeat unit is occupied by glutamine, and/or
(iii) the heptad f-position of the first heptad repeat unit is occupied by lysine, and/or
(iv) the heptad g-position of the first heptad repeat unit is occupied by glutamic acid, and/or
(v) the heptad b-position of the second heptad repeat unit is occupied by threonine, and/or
(vi) the heptad c-position of the second heptad repeat unit is occupied by threonine, and/or
(vii) HRS1 comprises a partial (a-c) heptad repeat unit following the third heptad repeat and the heptad c-position therein is occupied by threonine.

In further particular embodiments, the polypeptides are characterized in that in HRS3:
(i) the heptad b-position of the second heptad repeat unit is occupied by alanine, and/or
(ii) the heptad f-position of the second heptad repeat unit is occupied by glutamic acid, and/or
(iv) the heptad e-position of the fourth heptad repeat unit is occupied by valine, and/or
(v) HRS3 comprises a partial (a-f) heptad repeat unit following the third heptad repeat and the heptad f-position therein is occupied by serine.

Particular embodiments of the polypeptides envisaged herein are characterized in that the HRS1 has an amino acid sequence as defined in SEQ ID NO: 1 and/or the HRS3 has an amino acid sequence as defined in SEQ ID NO: 2.

The polypeptides envisaged herein can also be generally characterized in that the HRS1 and HRS3 of the HRS1-L1-HRS2-L2-HRS3 motif comprise
In the HRS1:
(i) the heptad f-position of the first heptad repeat unit is occupied by threonine or lysine,
(ii) the heptad g-position of the first heptad repeat unit is occupied by glutamine or glutamic acid,
(iii) the heptad f-position of the second heptad repeat unit is occupied by glutamic acid or alanine,
(iv) the heptad g-position of the second heptad repeat unit is occupied by valine,
(v) the heptad c-position of the third heptad repeat unit is occupied by alanine or glycine, and
(vi) the heptad g-position of the third heptad repeat unit is occupied by tyrosine or tryptophan, and
In addition, the amino acid sequences are characterized in that:
in the HRS3:
(i) the heptad b-position of the second heptad repeat unit is occupied by alanine or threonine,
(ii) the heptad e-position of the second heptad repeat unit is occupied by glutamine or lysine,
(iii) the heptad e-position of the third heptad repeat unit is occupied by tyrosine, and
(iv) HRS3 comprises a partial (a-f) heptad repeat unit following the third heptad repeat and the heptad b-position therein is occupied by methionine.

In still further particular embodiments, the polypeptides as envisaged herein are characterized in that they comprise a sequence corresponding to any one of SEQ ID NO's 3-22, respectively.

In certain particular embodiments, the polypeptides as envisaged herein comprise an amino acid sequence having at least 90% sequence identity with SEQ ID NO:3 or SEQ ID NO: 28. In particular embodiments, the polypeptides comprise an amino acid sequence as defined in SEQ ID NO: 3.

In a further aspect, the application provides polypeptides as envisaged herein for use as a medicament. In particular, the polypeptides as envisaged herein are for use in a method for the treatment and/or prevention of an IL-23-mediated disease chosen from the group consisting of inflammation and inflammatory disorders such as bowel diseases (colitis, Crohn's disease, IBD), infectious diseases, psoriasis, cancer, autoimmune diseases (such as MS), carcoidis, transplant rejection, cystic fibrosis, asthma, chronic obstructive pulmonary disease, rheumatoid arthritis, viral infection and common variable immunodeficiency.

In a further aspect, the application provides polypeptides as envisaged herein for use as a diagnostic. In particular, the polypeptides as envisaged herein are for use in a method for detecting aberrant expression or function of IL-23.

In still a further aspect, the application provides pharmaceutical compositions, which comprise a polypeptide as envisaged herein and a pharmaceutically acceptable carrier.

In a further aspect, the application provides nucleic acid sequences encoding the polypeptides as envisaged herein.

DETAILED DESCRIPTION OF THE INVENTION

Definitions

As used herein, the singular forms 'a', 'an', and the include both singular and plural referents unless the context clearly dictates otherwise.

The terms 'comprising', 'comprises' and 'comprised of' as used herein are synonymous with 'including', 'includes' or 'containing', 'contains', and are inclusive or open-ended and do not exclude additional, non-recited members, elements or method steps.

The recitation of numerical ranges by endpoints includes all numbers and fractions subsumed within the respective ranges, as well as the recited endpoints.

The term 'about' as used herein when referring to a measurable value such as a parameter, an amount, a temporal duration, and the like, is meant to encompass variations of +/−10% or less, preferably +/−5% or less, more preferably +/−1% or less, and still more preferably +1-0.1% or less of and from the specified value, insofar such variations are appropriate to perform in the disclosed invention. It is to be understood that the value to which the modifier 'about' refers is itself also specifically, and preferably, disclosed.

As used herein, an 'Alphabody' or 'Alphabodies' can generally be defined as sequences of amino acids which are single-chain, triple-stranded, predominantly alpha-helical, coiled coil amino acid sequences. More particularly, an Alphabody structure as used in the context of the present invention can be defined as an amino acid sequences having the general formula HRS1-L1-HRS2-L2-HRS3, wherein each of HRS1, HRS2 and HRS3 is independently a heptad repeat sequence (HRS) comprising or consisting of 2 to 7 consecutive but not necessarily identical heptad repeat units, at least 50% of all heptad a- and d-positions are occupied by isoleucine residues, each HRS starts with an aliphatic or aromatic amino acid residue located at a heptad a-position, particularly with an Isoleucine;

each of L1 and L2 are independently a linker fragment, as further defined hereinafter, which covalently connect HRS1 to HRS2 and HRS2 to HRS3, respectively.

In the Alphabody or Alphabody structure as defined above, HRS1, HRS2 and HRS3 will together form a triple-stranded, alpha-helical, coiled coil structure.

As used herein, a 'parallel Alphabody' refers to an Alphabody as defined above further characterized in that the alpha-helices of the triple-stranded, alpha-helical, coiled coil structure together form a parallel coiled coil structure, i.e., a coiled coil wherein all three alpha-helices are oriented in parallel.

As used herein, an 'antiparallel Alphabody' refers to an Alphabody as defined above further characterized in that the alpha-helices of the triple-stranded, alpha-helical, coiled coil structure together form an antiparallel coiled coil structure, i.e., a coiled coil wherein two alpha-helices are parallel and the third alpha-helix is antiparallel with respect to these two helices.

As will become clear from the further description herein, the application envisages polypeptides comprising an amino acid sequence with the general formula HRS1-L1-HRS2-L2-HRS3, but which in certain particular embodiments may comprise additional residues, moieties and/or groups, which are covalently linked, more particularly N- and/or C-terminal covalently linked, to a basic Alphabody sequence structure having the formula HRS1-L1-HRS2-L2-HRS3. Thus reference is made herein generally to '(Alphabody) polypeptides' which comprise or consist of an Alphabody as defined above, which may be covalently linked to additional sequences. The binding features described for an Alphabody herein can generally also be applied to polypeptides comprising said Alphabody.

The terms 'heptad', 'heptad unit' or 'heptad repeat unit' are used interchangeably herein and shall herein have the meaning of a 7-residue (poly)peptide motif that is repeated two or more times within each heptad repeat sequence of an Alphabody structure, and is represented as 'abcdefg' or 'defgabc', wherein the symbols 'a' to 'g' denote conventional heptad positions. As understood by the skilled person this implies that the consecutive heptad units within a repeat need not contain the same amino acids but will contain the same type of amino acid (hydrophobic vs. polar, as detailed below) at the same position. Conventional heptad positions are assigned to specific amino acid residues within a heptad, a heptad unit, or a heptad repeat unit, present in an Alphabody structure, for example, by using specialized software such as the COILS method of Lupas et al. (Science 1991, 252:1162-1164; http://www.russell.embl-heidelberg.de/cgi-bin/coils-svr.pl). However, it is noted that the heptads or heptad units as present in the Alphabody structure are not strictly limited to the above-cited representations (i.e. 'abcdefg' or 'defgabc') as will become clear from the further description herein and in their broadest sense constitute a 7-residue (poly)peptide fragment per se, comprising at least assignable heptad positions a and d.

The terms 'heptad a-positions', 'heptad b-positions', 'heptad c-positions', 'heptad d-positions', 'heptad e-positions', 'heptad f-positions' and 'heptad g-positions' refer respectively to the conventional 'a', 'b', 'c', 'd', 'e', 'f' and 'g' amino acid positions in a heptad, heptad repeat or heptad repeat unit.

A heptad motif (as defined herein) of the type 'abcdefg' is typically represented as 'HPPHPPP', whereas a 'heptad motif' of the type 'defgabc' is typically represented as 'HPPPHPP', wherein the symbol 'H' denotes an apolar or hydrophobic amino acid residue and the symbol 'P' denotes a polar or hydrophilic amino acid residue. Typical hydrophobic residues located at a- or d-positions include aliphatic (e.g., leucine, isoleucine, valine, methionine) or aromatic (e.g., phenylalanine) amino acid residues. Heptads within coiled coil sequences do not always comply with the ideal pattern of hydrophobic and polar residues, as polar residues are occasionally located at 'H' positions and hydrophobic residues at 'P' positions. Thus, the patterns 'HPPHPPP' and 'HPPPHPP' are to be considered as ideal patterns or characteristic reference motifs. Occasionally, the characteristic heptad motif is represented as 'HPPHCPC' or 'HxxHCxC' wherein 'H' and 'P' have the same meaning as above, 'C' denotes a charged residue (lysine, arginine, glutamic acid or aspartic acid) and denotes any (unspecified) natural amino acid residue. Since a heptad can equally well start at a d-position, the latter motifs can also be written as 'HCPCHPP' or 'HCxCHxx'. It is noted that single-chain Alphabodies are intrinsically so stable that they do not require the aid of ionic interactions between charged ('C') residues at heptad e- and g-positions.

A 'heptad repeat sequence' ('HRS') as used herein shall have the meaning of an amino acid sequence or sequence fragment comprising or consisting of n consecutive heptads, where n is a number equal to or greater than 2.

A heptad repeat sequence (HRS) can thus generally be represented by $(abcdefg)_n$, or $(defgabc)_n$, in notations referring to conventional heptad positions, or by $(HPPHPPP)_n$, or $(HPPPHPP)_n$, in notations referring to the heptad motifs, with the proviso that a) the amino acids at positions a-g or H and P need not be identical amino acids in the different heptads b) not all amino acid residues in a HRS should strictly follow the ideal pattern of hydrophobic and polar residues and c) the HRS may end with an incomplete or partial heptad motif. With regard to the latter, in particular embodiments, the HRS may contain an additional sequence "abc", "abcd", "abcde", or "abcdef" following c-terminally the (abcdefg)$_n$ sequence. However, in particular embodiments of the Alphabody structure as envisaged herein, a 'heptad repeat sequence' ('HRS') is an amino acid sequence or sequence fragment comprising n consecutive (but not necessarily identical) heptads generally represented by abcdefg or defgabc, where n is a number equal to or greater than 2, wherein at least 50% of all heptad a- and d-positions are occupied by isoleucine residues, each HRS starting with a full heptad sequence abcdefg or defgabc, and ending with a partial heptad sequence abcd or defga, such that each HRS starts and ends with an aliphatic or aromatic amino acid residue located at either a heptad a- or d-position.

In order to identify heptad repeat sequences, and/or their boundaries, these heptad repeat sequences comprising amino acids or amino acid sequences that deviate from the consensus motif, and if only amino acid sequence information is at hand, then the COILS method of Lupas et al. (Science 1991, 252:1162-1164) is a suitable method for the determination or prediction of heptad repeat sequences and their boundaries, as well as for the assignment of heptad positions. Furthermore, the heptad repeat sequences can be resolved based on knowledge at a higher level than the primary structure (i.e., the amino acid sequence). Indeed, heptad repeat sequences can be identified and delineated on the basis of secondary structural information (i.e. alpha-helicity) or on the basis of tertiary structural (i.e., protein folding) information. A typical characteristic of a putative HRS is an alpha-helical structure. Another (strong) criterion is the implication of a sequence or fragment in a coiled coil structure. Any sequence or fragment that is known to form a regular coiled coil structure, i.e., without stutters or stammers as described in Brown et al. Proteins 1996, 26:134-145, is herein considered a HRS. Also and more particularly, the identification of HRS fragments can be based on high-resolution 3-D structural information (X-ray or NMR structures). Finally, in particular embodiments, the boundaries to an HRS fragment may be defined as the first a- or d-position at which a standard hydrophobic amino acid residue (selected from the group valine, isoleucine, leucine, methionine, phenylalanine, tyrosine or tryptophan) is located. In particular embodiments, the boundaries to an HRS fragment can be defined by the presence of an isoleucine amino acid residue.

In the context of the single-chain structure of the Alphabodies (as defined herein) the terms 'linker', 'linker fragment' or 'linker sequence' are used interchangeably herein and refer to an amino acid sequence fragment that is part of the contiguous amino acid sequence of a single-chain Alphabody, and which covalently interconnect the HRS sequences of that Alphabody structure.

The linkers within a single-chain structure of the Alphabodies (as defined herein) thus interconnect the HRS sequences, and more particularly the first to the second HRS, and the second to the third HRS in an Alphabody structure. Each linker sequence in an Alphabody structure commences with the residue following the last heptad residue of the preceding HRS and ends with the residue preceding the first heptad residue of the next HRS. Connections between HRS fragments via disulfide bridges or chemical cross-linking or, in general, through any means of inter-chain linkage (as opposed to intra-chain linkage), are explicitly excluded from the definition of a linker fragment (at least, in the context of an Alphabody) because such would be in contradiction with the definition of a single-chain Alphabody. A linker fragment in an Alphabody structure is preferably flexible in conformation to ensure relaxed (unhindered) association of the three heptad repeat sequences as an alpha-helical coiled coil structure. Further in the context of an Alphabody, 'L1' shall denote the linker fragment one, i.e., the linker between HRS1 and HRS2, whereas 'L2' shall denote the linker fragment two, i.e., the linker between HRS2 and HRS3. Suitable linkers for use in the polypeptides envisaged herein will be clear to the skilled person, and may generally be any linker used in the art to link amino acid sequences, as long as the linkers are structurally flexible, in the sense that they do not affect the characteristic three dimensional coiled coil structure of the Alphabody. The two linkers L1 and L2 in a particular Alphabody structure, may be the same or may be different. Based on the further disclosure herein, the skilled person will be able to determine the optimal linkers, optionally after performing a limited number of routine experiments. In particular embodiments, the linkers L1 and L2 are amino acid sequences consisting of at least 4, in particular at least 8, more particularly at least 12 amino acid residues, with a non-critical upper limit chosen for reasons of convenience being about 30 amino acid residues. In a particular, non-limiting embodiment, preferably at least 50% of the amino acid residues of a linker sequence are selected from the group proline, glycine, and serine. In further non-limiting embodiments, preferably at least 60%, such as at least 70%, such as for example 80% and more particularly 90% of the amino acid residues of a linker sequence are selected from the group proline, glycine, and serine. In other particular embodiments, the linker sequences essentially consist of polar amino acid residues; in such particular embodiments, preferably at least 50%, such as at least 60%, such as for example 70% or 80% and more particularly 90% or up to 100% of the amino acid residues of a linker sequence are selected from the group consisting of glycine, serine, threonine, alanine, proline, histidine, asparagine, aspartic acid, glutamine, glutamic acid, lysine and arginine.

In the present application, reference to a 'coiled coil' or 'coiled coil structure' shall be used interchangeably herein and will be clear to the person skilled in the art based on the common general knowledge and the description and further references cited herein. Particular reference in this regard is made to review papers concerning coiled coil structures, such as for example, Cohen and Parry *Proteins* 1990, 7:1-15; Kohn and Hodges *Trends Biotechnol* 1998, 16:379-389; Schneider et al *Fold Des* 1998, 3:R29-R40; Harbury et al. *Science* 1998, 282:1462-1467; Mason and Arndt *ChemBioChem* 2004, 5:170-176; Lupas and Gruber *Adv Protein Chem* 2005, 70:37-78; Woolfson *Adv Protein Chem* 2005, 70:79-112; Parry et al. *J Struct Biol* 2008, 163:258-269; McFarlane et al. *Eur J Pharmacol* 2009:625:101-107.

A 'solvent-oriented' or 'solvent-exposed' region of an alpha-helix of an Alphabody structure shall herein have the meaning of that part on an Alphabody structure which is directly exposed or which comes directly into contact with the solvent, environment, surroundings or milieu in which it is present. The solvent-oriented region is largely formed by b-, c- and f-residues. There are three such regions per single-chain Alphabody, i.e., one in each alpha-helix. Any part of such solvent-oriented region is also considered a solvent-oriented region. For example, a sub-region composed of the b-, c- and f-residues from three consecutive heptads in an Alphabody alpha-helix will also form a solvent-oriented surface region.

The term 'groove of an Alphabody' shall herein have the meaning of that part on an Alphabody of a polypeptide as envisaged herein which corresponds to the concave, groove-like local shape, which is formed by any pair of spatially adjacent alpha-helices within said Alphabody. Residues implicated in the formation of (the surface of) a groove between two adjacent alpha-helices in an Alphabody are generally located at heptad e- and g-positions, but some of the more exposed b- and c-positions as well as some of the largely buried core a- and d-positions may also contribute to a groove surface; such will essentially depend on the size of the amino acid side-chains placed at these positions. If the said spatially adjacent alpha-helices run parallel, then one half of the groove is formed by b- and e-residues from a first helix and the second half by c- and g-residues of the second helix. If the said spatially adjacent alpha-helices are antiparallel, then there exist two possibilities. In a first possibility, both halves of the groove are formed by b- and e-residues. In the second possibility, both halves of the groove are formed by c- and g-residues. The three types of possible grooves are herein denoted by their primary groove-forming (e- and g-) residues: if the helices are parallel, then the groove is referred to as an e/g-groove; if the helices are antiparallel, then the groove is referred to as either an e/e-groove or a g/g-groove. Parallel Alphabodies have three e/g-grooves, whereas antiparallel Alphabodies have one e/g-groove, one e/e-groove and one g/g-groove. Any part of an Alphabody groove is also considered a groove region.

As used herein, amino acid residues will be indicated either by their full name or according to the standard three-letter or one-letter amino acid code.

As used herein, the term 'homology' denotes at least secondary structural similarity between two macromolecules, particularly between two polypeptides or polynucleotides, from same or different taxons, wherein said similarity is due to shared ancestry. Hence, the term 'homologues' denotes so-related macromolecules having said secondary and optionally tertiary structural similarity. For comparing two or more nucleotide sequences, the '(percentage of) sequence identity' between a first nucleotide sequence and a second nucleotide sequence may be calculated using methods known by the person skilled in the art, e.g. by dividing the number of nucleotides in the first nucleotide sequence that are identical to the nucleotides at the corresponding positions in the second nucleotide sequence by the total number of nucleotides in the first nucleotide sequence and multiplying by 100% or by using a known computer algorithm for sequence alignment such as NCBI Blast. In determining the degree of sequence identity between two Alphabodies, the skilled person may take into account so-called 'conservative' amino acid substitutions, which can generally be described as amino acid substitutions in which an amino acid residue is replaced with another amino acid residue of similar chemical structure and which has little or essentially no influence on the function, activity or other biological properties of the polypeptide. Possible conservative amino acid substitutions will be clear to the person skilled in the art. Alphabodies and nucleic acid sequences are said to be 'exactly the same' if they have 100% sequence identity over their entire length.

A polypeptide (or the Alphabody structure comprised therein) is said to 'specifically bind to' a particular target when that polypeptide has affinity for, specificity for, and/or is specifically directed against that target (or against at least one part or fragment thereof).

The 'specificity' of an anti-IL23 polypeptide as used herein can be determined based on affinity and/or avidity. The 'affinity' of a polypeptide is represented by the equilibrium constant for the dissociation of the polypeptide and IL-23. The lower the KD value, the stronger the binding strength between the polypeptide and IL-23. Alternatively, the affinity can also be expressed in terms of the affinity constant (KA), which corresponds to 1/KD. The binding affinity of an anti-IL23 polypeptide can be determined in a manner known to the skilled person, depending on the specific target protein of interest. It is generally known in the art that the KD can be expressed as the ratio of the dissociation rate constant of a complex, denoted as kOff (expressed in seconds$^{-1}$ or s$^{-1}$), to the rate constant of its association, denoted kOn (expressed in molar$^{-1}$ seconds$^{-1}$ or M$^{-1}$ s$^{-1}$). A KD value greater than about 1 millimolar is generally considered to indicate non-binding or non-specific binding.

The 'avidity' of an anti-IL23 polypeptide is the measure of the strength of binding between said polypeptide and IL-23. Avidity is related to both the affinity between a binding site on IL-23 and a binding site on the Alphabody within the polypeptide and the number of pertinent binding sites present on the Alphabody.

An anti-IL23 polypeptide as envisaged herein is said to be 'specific for a first target protein of interest as opposed to a second target protein of interest' when it binds to the first target protein of interest with an affinity that is at least 5 times, such as at least 10 times, such as at least 100 times, and preferably at least 1000 times higher than the affinity with which that polypeptide binds to the second target protein of interest. Accordingly, in certain embodiments, when a polypeptide is said to be 'specific for' a first target protein of interest as opposed to a second target protein of interest, it may specifically bind to (as defined herein) the first target protein of interest, but not to the second target protein of interest.

The 'half-life' of an anti-IL23 polypeptide can generally be defined as the time that is needed for the in vivo serum or plasma concentration of the polypeptide to be reduced by 50%. The in vivo half-life of an anti-IL23 polypeptide can be determined in any manner known to the person skilled in the art, such as by pharmacokinetic analysis. As will be clear to the skilled person, the half-life can be expressed using parameters such as the t1/2-alpha, t1/2-beta and the area under the curve (AUC). An increased half-life in vivo is generally characterized by an increase in one or more and preferably in all three of the parameters t1/2-alpha, t1/2-beta and the area under the curve (AUC).

As used herein, the terms 'inhibiting', 'reducing' and/or 'preventing' may refer to (the use of) an anti-IL23 polypeptide that specifically binds to IL-23 and inhibits, reduces and/or prevents the interaction between IL-23 and its receptor An anti-IL23 polypeptide is said to show 'cross-reactivity' for two different target proteins of interest if it is specific for (as defined herein) both of these different target proteins of interest.

As used herein, the term 'prevention and/or treatment' comprises preventing and/or treating a certain disease and/or disorder, preventing the onset of a certain disease and/or disorder, slowing down or reversing the progress of a certain disease and/or disorder, preventing or slowing down the onset of one or more symptoms associated with a certain disease and/or disorder, reducing and/or alleviating one or more symptoms associated with a certain disease and/or disorder, reducing the severity and/or the duration of a certain disease and/or disorder, and generally any prophylactic or therapeutic effect of the Alphabodies of the invention that is beneficial to the subject or patient being treated.

All documents cited in the present specification are hereby incorporated by reference in their entirety. Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

INVENTION RELATED DESCRIPTION

The present inventors have identified polypeptides that specifically bind to IL-23. More particularly, the application provides polypeptides comprising at least one Alphabody sequence, that specifically binds to IL-23, more particularly to the p19 subunit of IL-23. In addition, it has been found that the IL-23 binding polypeptides not only bind to IL-23 with affinities lying in the subnanomolar range but are capable of neutralizing the biological activity of IL-23.

Moreover, the IL-23-binding polypeptides as envisaged herein, which comprise an amino acid sequence of at least one Alphabody, maintain the advantages identified for Alphabody scaffolds. Alphabodies not only have a unique structure but also have several advantages over the traditional (immunoglobulin and non-immunoglobulin) scaffolds known in the art. These advantages include, but are not limited to, the fact that they are compact and small in size (between 10 and 14 kDa, which is 10 times smaller than an antibody), they are extremely thermostable (i.e., they generally have a melting temperature of more than 100° C.), they can be made resistant to different proteases, they are highly engineerable (in the sense that multiple substitutions will generally not obliterate their correct and stable folding), and have a structure which is based on natural motifs which have been redesigned via protein engineering techniques. Finally, it has been observed that the polypeptides envisaged herein have a reduced immunogenicity compared to known antibody IL-23 binders (such as Ustekinumab).

The application thus provides polypeptides comprising an amino acid sequence that is capable of specifically binding to the heterodimeric cytokine IL-23 and are capable of neutralizing its biological activity, as determined in the assays described herein. The polypeptides as envisaged herein comprise an amino acid sequence, which corresponds to the structural motif of an Alphabody. Accordingly, the polypeptides as envisaged herein comprise an amino acid sequence having the general formula

HRS1-L1-HRS2-L2-HRS3, wherein each of HRS1, HRS2 and HRS3 is independently a heptad repeat sequence (HRS) comprising or consisting of 2 to 7 consecutive heptad repeat units, wherein said heptad repeat units are 7-residue (poly) peptide fragments represented as 'abcdefg' or 'defgabc', wherein the symbols 'a' to 'g' denote conventional heptad positions, wherein at least 50% of all heptad a- and d-positions are occupied by isoleucine residues, wherein each HRS starts with an aliphatic or aromatic amino acid residue located at a heptad a position, wherein each of L1 and L2 are independently a linker fragment, which covalently connect HRS1 to HRS2 and HRS2 to HRS3, respectively.

It has been found that specific sequence motifs within the Alphabody structure, and more particularly within HRS1 and HRS3 thereof are capable of neutralizing the activity of target IL-23. The presence of this sequence motif ensures a binding to IL-23 which ensures a neutralizing effect not observed in previously described IL-23 targeting Alphabodies (such as those disclosed in WO2012/093172).

The improved properties of the Alphabodies can be attributed to the presence of specific amino acids at specific positions in the HRS1 and/or HRS3 of the Alphabodies. More particularly, it has been found that
in HRS1:
  (i) the heptad f-position of the second heptad repeat unit is occupied by glutamic acid or alanine,
  (ii) the heptad g-position of the second heptad repeat unit is occupied by valine,
  (iii) the heptad c-position of the third heptad repeat unit is occupied by alanine or glycine, and
  (iv) the heptad g-position of the third heptad repeat unit is occupied by tyrosine or tryptophan, and
in HRS3:
  (i) the heptad e-position of the second heptad repeat unit is occupied by glutamine or lysine,
  (ii) the heptad b-position of the third heptad repeat unit is occupied by leucine or isoleucine or valine,
  (iii) the heptad e-position of the third heptad repeat unit is occupied by tyrosine, and that
  (iv) HRS3 comprises a partial (a-f) heptad repeat unit following the third heptad repeat and the heptad b-position therein is occupied by methionine.

Indeed it has surprisingly been found that a relatively limited number of amino acid positions contribute significantly to the binding to IL-23.

The positions of the amino acids in the identified motif can be referred to by indicating the position (a-b-c-d-e-f-g) in the relevant (partial) heptad (1-2-...) within either HRS1 or HRS3 of the Alphabody structure. Thus, where HRS1 is characterized by the presence of at least three heptads with positions 1a1b1c1d1e1f1g, 2a2b2c2d2e2f2g, and 3a3b3c3d3e3f3g, the identified motif for HRS1 can also be presented as:
For HRS1:
  (i) position 2f is occupied by glutamic acid or alanine,
  (ii) position 2g is occupied by valine,
  (iii) position 3c is occupied by alanine or glycine, and
  (iv) position 3g is occupied by tyrosine or tryptophan.

Similarly, where HRS3 is characterized by the presence of least three heptads with positions 1a1b1c1d1e1f1g, 2a2b2c2d2e2f2g and 3a3b3c3d3e3f3g and the identified motif for HRS3 can also be presented as:
For HRS3:
  (i) position 2e is occupied by glutamine or lysine,
  (ii) position 3b is occupied by leucine or isoleucine or valine,
  (iii) position 3e is occupied by tyrosine, and
  (iv) whereby in addition HRS3 comprises a partial heptad (a-f) following the third heptad wherein position 4b is occupied by methionine.

As indicated above, it has been determined based on the different Alphabodies obtained that in specific positions, limited variations are possible with only limited impact on the properties of the resulting polypeptides. However it has been established that polypeptides with improved properties are obtained when in HRS1:
  (i) position 2f is occupied by glutamic acid, and/or
  (ii) position 2g is occupied by valine, and/or
  (iii) position 3c is occupied by alanine, and/or
  (iv) position 3g is occupied by tyrosine Similarly it has been observed that polypeptides with improved properties are obtained when in HRS3 comprising a partial (a-f) heptad following the third heptad:
  (i) position 2e is occupied by glutamine, and/or
  (ii) position 3b is occupied by valine, and/or
  (ii) position 3e is occupied by tyrosine, and/or
  (iii) position 4b is occupied by methionine.

While the remaining positions within the Alphabody structure of the polypeptides envisaged herein are considered to be of lesser importance, it can be noted that in particular embodiments, the polypeptides envisaged herein are further characterized in that in HRS1:
  (i) position 1b is occupied by glutamine, glutamic acid or lysine and/or
  (ii) position 1c is occupied by glutamine, glutamic acid or lysine and/or
  (iii) position 1f is occupied by threonine or lysine, and/or
  (iv) position 1g is occupied by glutamine or glutamic acid, and/or
  (v) position 2b is occupied by threonine, alanine or lysine, and/or
  (vi) position 2c is occupied by threonine, glutamine, asparagine or serine, and/or
  (vii) HRS1 comprises a partial heptad (a-c) following the third heptad wherein the 4c-position is occupied by threonine, arginine, glycine, serine, leucine or methionine;
And/or that in HRS3 comprising a partial (a-f) heptad following the third heptad:
  (i) position 2b is occupied by alanine or threonine, and/or
  (ii) position 2f is occupied by by glutamic acid, glycine, aspartic acid, alanine, asparagine or arginine, and/or
  (iii) position 4e is occupied by alanine, valine, serine, proline, glycine, lysine or threonine, and/or
  (iv) position 4f is occupied by serine, threonine, arginine, aspartic acid, glutamine, isoleucine, glycine, leucine or proline.

It has been determined that the remaining positions of the Alphabody structure of the polypeptides are even less critical. More particularly, it has been found that in the polypeptides having improved properties as envisaged herein, the sequence of the HRS2 heptad repeat is of limited importance. Purely exemplary sequences of HRS2 correspond to the HRS2 sequences provided in SEQ ID NO: 27 present in polypeptides 1-20 of FIG. 1.

In particular embodiments, polypeptides are provided wherein HRS1 has an amino acid sequence as defined in SEQ ID NO 1 (IEQIQKEITT IQEVIAAIQK YIYTM). In further particular embodiments, HRS3 has an amino acid sequence as defined in SEQ ID NO. 2 (IEEIQKQIAA IQEQIVAIYK QIMAM). In further particular embodiments, polypeptides are provided comprising a sequence selected from SEQ ID NOs. 3 to 22 (FIG. 1).

The polypeptides envisaged herein contain linkers connecting the subsequent heptad repeat sequences HRS1, HRS2, HRS3. It is envisaged that the nature of the linker is not critical with regard to the binding properties of the polypeptides envisaged herein. In particular embodiments, the linker sequences are Glycine and Serine-rich sequences with a minimum length of about 8 amino acids. In particular embodiments the linkers comprise 1 or 2 repeats of a "Glycine/Serine-rich" sequence such as GGSGGSGG (SEQ ID NO. 23) or GSGGGGSG (SEQ ID NO. 24). The linker connecting HRS1 and HRS2, referred to as "linker1" may be the same or different from the linker connecting HRS2 and HRS3, referred to as "linker2". In particular embodiments, linker 1 is (GGSGGSGG)n, wherein n=1 or 2 and linker2 is (GSGGGGSG)n, wherein n=1 or 2. Such linkers need not be composed only of Gly/Ser residues and in addition typically contain one or more amino acids N- and/or C-terminally thereof. Such linkers include, but are note limited to MTGGSGGSGGMS (SEQ ID NO: 25) and MTGGSGGSGGGGSGGSGGMS (SEQ ID NO: 26). In particular embodiments, the polypeptides envisaged herein are derived from a polypeptide sequence provided in SEQ ID NO:28 (MSIEQIQKEITTIQEVIAAIQKYIYT-MTGGSGGSGGMSIEEIQKQIAAIQEQIAAIQKQI-YAMTGSGGG GSGMSIEEIQKQIAAIQEQIVAIYKQI-MAMASAAAHHHHHH), which has been modified in one or more amino acid positions to increase expression in a bacterial system, to remove a c-terminal tail (3Ala-6His), to optimize solubility, and/or to optimize binding affinity. In particular embodiments, the polypeptides envisaged herein have at least 85% sequence identity, preferably at least 90% sequence identity with SEQ ID NO:28. In particular embodiments, the sequence identity determined taking into account only the amino acids which are part of the heptad repeat sequences of the Alphabody structure is at least 80%, more preferably at least 85%, or at least 90% as compared to SEQ ID NO: 28. In particular embodiments, the sequence identity with SEQ ID NO:28 at the HRS levels is at least 95%.

The polypeptides as envisaged herein may comprise at least one sequence comprising an Alphabody structure and optionally one or more further groups, moieties, residues optionally linked via one or more linkers.

In particular embodiments, the polypeptides of the present invention comprise Alphabodies that have been chemically modified to increase the biological or plasma half-life thereof, by means of the addition of a group which binds to or which is a serum protein (such as serum albumin) or, in general, by linkage of the Alphabody sequence to a moiety that increases the half-life of the Alphabody of the invention. As an example, polypeptides, and more particularly the Alphabody sequences comprised therein can be PEGylated at a solvent exposed cysteine using maleimide mPEG 40 kD PEG (Jenkem Technology) or other PEG moieties of different molecular mass. The PEGylation of Alphabodies is also described in WO2012/093172.

In particular embodiments, the polypeptides of the present invention comprise Alphabodies that have been fused to protein domains or peptides to increase the biological or plasma half-life thereof, for example, with a domain which binds to or which is a serum protein (such as serum albumin or to the Fc part of an immunoglobulin). Said protein domain may be an Alphabody which binds to a serum protein.

In particular embodiments, the polypeptides of the present invention comprise Alphabodies that in addition to their target binding (i.e., binding toward the cytokine or growth factor or cytokine or growth factor receptor of interest) bind also to a serum protein (such as serum albumin or to the Fc part of an immunoglobulin) to increase the biological or plasma half-life of said Alphabodies.

In particular embodiments, the polypeptides as envisaged herein thus may optionally contain one or more further groups, moieties or residues for binding to other targets or target proteins of interest. It should be clear that such further groups, residues, moieties and/or binding sites may or may not provide further functionality to the Alphabodies as envisaged herein (and/or to the polypeptide or composition in which it is present) and may or may not modify the properties of the Alphabody as envisaged herein. Such groups, residues, moieties or binding units may also for example be chemical groups which can be biologically and/or pharmacologically active.

These groups, moieties or residues are, in particular embodiments, linked N- or C-terminally to the Alphabody. In particular embodiments however, one or more groups, moieties or residues are linked to the body of the Alphabody, e.g. to a free cysteine in an alpha-helix.

The polypeptides envisaged herein may further comprise additional amino acids or moieties covalently bound to the sequence corresponding to HRS1-L1-HRS2-L2-HRS3. In particular embodiments, the polypeptides may comprise 1-5 amino acids N- and/or C-terminally attached to the first heptad repeat of HRS1 or the last heptad repeat of HRS3. In particular embodiments, the polypeptides comprise 2 amino-acids linked N- and C-terminally to the Alphabody structure.

Additionally or alternatively, as detailed above, where the 'HRS' is considered to consist only of heptad repeat units, the polypeptides as envisaged herein may typically comprise an additional partial sequence of a heptad repeat (a-d) c-terminally attached to the last heptad repeat of HRS3.

Exemplary polypeptides comprising additional amino acids include SEQ ID NOs: 3-22.

Additionally or alternatively, the optional N and C extensions can be, for example, a tag for detection or purification (e.g., a His-tag) or another protein or protein domain, in which case the full construct is denoted a fusion protein. For the sake of clarity, the optional extensions N and C are herein considered not to form part of a single-chain Alphabody structure, which is defined by the general formula 'HRS1-L1-HRS2-L2-HRS3'.

In particular embodiments, the polypeptides of the present invention comprise amino acids that have been chemically modified. For example, such a modification may involve the introduction or linkage of one or more functional groups, residues or moieties into or onto the amino acid sequence. These groups, residues or moieties may confer one or more desired properties or functionalities to the polypeptides. Examples of such functional groups will be clear to the skilled person as detailed below.

For example, the introduction or linkage of such functional groups in a polypeptide as envisaged herein can result in an increase in the half-life, the solubility and/or the stability of the polypeptide or in a reduction of the toxicity of the polypeptide, or in the elimination or attenuation of any undesirable side effects of the polypeptide, and/or in other advantageous properties.

Typically, the polypeptides as envisaged herein with increased half-life have a half-life (in human or in an animal model used for PK evaluation such as rat, dog, monkey, mouse, horse, pig, cat, etc) of more than 1 week, equally preferably more than 2 weeks as compared to the half-life of the corresponding polypeptide lacking the above described equipment for half life extension.

A particular modification of the polypeptides envisaged herein may comprise the introduction of one or more detectable labels or other signal-generating groups or moieties, depending on the intended use of the labeled polypeptide.

Yet a further particular modification may involve the introduction of a chelating group, for example to chelate one or more metals or metallic cations.

A particular modification may comprise the introduction of a functional group that is one part of a specific binding pair, such as the biotin-(strept)avidin binding pair.

For some applications, in particular for those applications in which it is intended to kill a cell that expresses IL-23, or to reduce or slow the growth and/or proliferation of such a cell, the polypeptides envisaged herein may also be linked to a toxin or to a toxic residue or moiety.

Other potential chemical and enzymatic modifications will be clear to the skilled person.

In further particular embodiments, the polypeptides envisaged herein comprise amino acid sequences corresponding to two or more target-specific Alphabodies. The combination of two Alphabody structures directed against the target IL-23 may further improve binding properties to IL-23.

In such particular embodiments, the two or more target-specific Alphabodies may be linked (coupled, concatenated, interconnected, fused) to each other either in a direct or in an indirect way. In embodiments wherein the two or more Alphabodies are directly linked to each other, they are linked without the aid of a spacer or linker fragment or moiety. Alternatively, in embodiments wherein the two or more Alphabodies are indirectly linked to each other, they are linked via a suitable spacer or linker fragment or linker moiety.

In embodiments wherein two or more Alphabodies are directly linked, they may be produced as single-chain fusion constructs (i.e., as single-chain protein constructs wherein two or more Alphabody sequences directly follow each other in a single, contiguous amino acid sequence). Alternatively, direct linkage of Alphabodies may also be accomplished via cysteines forming a disulfide bridge between two Alphabodies (i.e., under suitable conditions, such as oxidizing conditions, two Alphabodies comprising each a free cysteine may react with each other to form a dimer wherein the constituting momomers are covalently linked through a disulfide bridge).

Alternatively, in embodiments wherein two or more Alphabodies are indirectly linked, they may be linked to each other via a suitable spacer or linker fragment or linker moiety. In such embodiments, they may also be produced as single-chain fusion constructs (i.e., as single-chain protein constructs wherein two or more Alphabody sequences follow each other in a single, contiguous amino acid sequence, but wherein the Alphabodies remain separated by the presence of a suitably chosen amino acid sequence fragment acting as a spacer fragment). Alternatively, indirect linkage of Alphabodies may also be accomplished via amino acid side groups or via the Alphabody N- or C-termini. For example, under suitably chosen conditions, two Alphabodies comprising each a free cysteine may react with a homo-bifunctional chemical compound, yielding an Alphabody dimer wherein the constituting Alphabodies are covalently cross-linked through the said homo-bifunctional compound. Analogously, one or more Alphabodies may be cross-linked through any combination of reactive side groups or termini and suitably chosen homo- or heterobifunctional chemical compounds for cross-linking of proteins.

In particular embodiments of linked Alphabodies, the two or more linked Alphabodies can have the same amino acid sequence or different amino acid sequences. The two or more linked Alphabodies can also have the same binding specificity or a different binding specificity. The two or more linked Alphabodies can also have the same binding affinity or a different binding affinity.

Suitable spacers or linkers for use in the coupling of different Alphabodies will be clear to the skilled person and may generally be any linker or spacer used in the art to link peptides and/or proteins. In particular, such a linker or spacer is suitable for constructing proteins or polypeptides that are intended for pharmaceutical use.

Some particularly suitable linkers or spacers for coupling of Alphabodies in a single-chain amino acid sequence include for example, but are not limited to, polypeptide linkers such as glycine linkers, serine linkers, mixed glycine/serine linkers, glycine- and serine-rich linkers or linkers composed of largely polar polypeptide fragments. Some particularly suitable linkers or spacers for coupling of Alphabodies by chemical cross-linking include for example, but are not limited to, homo-bifunctional chemical cross-linking compounds such as glutaraldehyde, imidoesters such as dimethyl adipimidate (DMA), dimethyl suberimidate (DMS) and dimethyl pimelimidate (DMP) or N-hydroxysuccinimide (NHS) esters such as dithiobis(succinimidylpropionate) (DSP) and dithiobis(sulfosuccinimidylpropionate) (DTSSP). Examples of hetero-bifunctional reagents for cross-linking include, but are not limited to, cross-linkers with one amine-reactive end and a sulfhydryl-reactive moiety at the other end, or with a NHS ester at one end and an SH-reactive group (e.g., a maleimide or pyridyl disulfide) at the other end.

A polypeptide linker or spacer for usage in single-chain concatenated Alphabody constructs may be any suitable (e.g., glycine-rich) amino acid sequence having a length between 1 and 50 amino acids, such as between 1 and 30, and in particular between 1 and 10 amino acid residues. It should be clear that the length, the degree of flexibility and/or other properties of the spacer(s) may have some influence on the properties of the final polypeptide of the invention, including but not limited to the affinity, specificity or avidity for a protein of interest, or for one or more other target proteins of interest. It should be clear that when two or more spacers are used in the polypeptides of the invention, these spacers may be the same or different. In the context and disclosure of the present invention, the person skilled in the art will be able to determine the optimal spacers for the purpose of coupling Alphabodies of the invention without any undue experimental burden.

The polypeptides as envisaged herein comprise an amino acid sequence that is capable of specifically binding to the heterodimeric cytokine IL-23. More particularly, the Alphabodies envisaged herein is specific for the p19 subunit of IL-23. Such polypeptides have advantages for prophylactic, therapeutic and/or diagnostic applications compared to binding agents that specifically bind to the p40 subunit of IL-23.

The polypeptides as envisaged herein will bind to IL-23 with a dissociation constant (KD) of less than about 1 nanomolar (1 nM) [i.e., with an association constant (KA) of about 1,000,000,000 per molar ($10^9$ M$^{-1}$, 1E9/M) or more]. A KD value greater than about 1 millimolar is generally considered to indicate non-binding or non-specific binding. It is generally known in the art that the KD can also be expressed as the ratio of the dissociation rate constant of a complex, denoted as kOff (expressed in seconds$^{-1}$ or s$^{-1}$), to the rate constant of its association, denoted kOn (expressed in molar$^{-1}$ seconds$^{-1}$ or M$^{-1}$ s$^{-1}$). In particular, the polypeptides as envisaged herein will bind to IL-23 with a kOff ranging between 0.001 and 0.0001 s$^{-1}$ and/or a kOn ranging between 100,000 and 1,000,000 M$^{-1}$ s$^{-1}$. Binding affinities, kOff and kOn rates may be determined by means of methods known to the person skilled in the art, for example ELISA methods, isothermal titration calorimetry, surface plasmon resonance, fluorescence-activated cell sorting analysis, and the more.

The polypeptides envisaged herein that specifically bind to IL-23, are moreover capable of specifically inhibiting, preventing or decreasing the activity of IL-23, and/or of inhibiting, preventing or decreasing the signaling and biological mechanisms and pathways in which IL-23 plays a role. Indeed by binding to IL-23, the polypeptides envisaged herein can prevent or inhibit the interaction between IL-23 and its receptor. Accordingly, the polypeptides and pharmaceutical compositions comprising said polypeptides envisaged herein can be used to affect, change or modulate the immune system and/or immune-mediated inflammatory disorders.

More particularly, 'inhibiting', 'reducing' and/or 'preventing' using the polypeptides envisaged herein may mean either inhibiting, reducing and/or preventing the interaction between IL-23 and its receptor and/or preventing one or more biological or physiological mechanisms, effects, responses, functions pathways or activities in IL-23 is involved, such as by at least 10%, but preferably at least 20%, for example by at least 50%, at least 60%, at least 70%, at least 80%, at least 90%, at least 95% or more, as measured using a suitable in vitro, cellular or in vivo assay, compared to the activity of IL-23 in the same assay under the same conditions but without using said polyeptide.

[Pharmaceutical Compositions]

The application also provides pharmaceutical compositions comprising one or more polypeptides and/or nucleic acid sequences as envisaged herein and optionally at least one pharmaceutically acceptable carrier (also referred to herein as pharmaceutical compositions of the invention). According to certain particular embodiments, the pharmaceutical compositions of the invention may further optionally comprise at least one other pharmaceutically active compound.

The pharmaceutical can be used in the diagnosis, prevention and/or treatment of diseases and disorders associated with IL-23, as described herein.

In particular, the present invention provides pharmaceutical compositions comprising polypeptides as envisaged herein that are suitable for prophylactic, therapeutic and/or diagnostic use in a warm-blooded animal, and in particular in a mammal. In particular embodiments, the mammal is a human, but veterinary purposes are also envisaged.

Generally, for pharmaceutical use, the polypeptides envisaged herein may be formulated as a pharmaceutical preparation or compositions comprising at least one polypeptide as envisaged herein and at least one pharmaceutically acceptable carrier, diluent or excipient and/or adjuvant, and optionally one or more further pharmaceutically active polypeptides and/or compounds. Such a formulation may be suitable for oral, parenteral, topical administration or for administration by inhalation. Thus, the compositions envisaged herein can for example be administered orally, intraperitoneally, intravenously, subcutaneously, intramuscularly, transdermally, topically, by means of a suppository, by inhalation, again depending on the specific pharmaceutical formulation or composition to be used.

The pharmaceutical compositions may also contain suitable binders, disintegrating agents, sweetening agents or flavoring agents. Tablets, pills, or capsules may be coated for instance with gelatin, wax or sugar and the like. In addition, the compositions may be formulated and/or administered using sustained-release formulations and devices.

The compositions envisaged herein will be administered in an amount which will be determined by the medical practitioner based inter alia on the severity of the condition and the patient to be treated. Typically, for each disease indication an optical dosage will be determined specifying the amount to be administered per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment.

In particular, the polypeptides envisaged herein may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

[Prophylactic, Therapeutic and/or Diagnostic Applications]

Also envisaged herein is the use of the polypeptides envisaged herein for the preparation of a medicament for the prevention and/or treatment of at least one IL-23-mediated disease and/or disorder. Accordingly, the invention provides compositions comprising the polypeptides envisaged herein for use in the prevention and/or treatment of at least one IL-23-mediated disease and/or disorder. In particular embodiments, the methods for the prevention and/or treatment of an IL-23-mediated disease and/or disorder comprise administering to a subject in need thereof, a pharmaceutically active amount of one or more polypeptides and/or pharmaceutical compositions as envisaged herein.

The subject or patient to be treated is in particular a mammal, and more in particular a human suffering from, or at risk of and IL-23-mediated disease or disorder. Examples of IL-23 mediated diseases and disorders include disorders of the immune system and immune-mediated inflammatory disorders such as psioriasis, bowel diseases (colitis, Crohn's disease, IBD), infectious diseases, and other autoimmune diseases (such as rheumatoid arthritis, Multiple Sclerosis, Spondyloarthritis, Sarcoidosis, Lupus, Behcet's disease), transplant rejection, cystic fibrosis, asthma, chronic obstructive pulmonary disease, cancer, viral infection, common variable immunodeficiency.

The efficacy of the Alphabodies and polypeptides of the invention, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person. For example the efficacy of an anti-IL-23 Alphabody or Alphabody polypeptide can be easily determined in an in vitro assay which measures the IL-23-dependent production of IL-17 in mouse splenocytes. In this assay, splenocytes from balb/c mice are isolated, and IL-23 (mouse or human) is added together with (or without) the selected Alphabodies or Alphabody polypeptides at various concentrations. The appearance of IL-17A in the supernatans will then be detected via an ELISA from which the inhibitory potential of the anti-IL-23 Alphabodies can be easily determined.

For example, the efficacy of an anti-IL-23 polypeptide can be determined in a mouse psoriasis model, using for example TNO's (The Netherlands) xenografted mice model which comprises following steps as described in TNO's web publication ('Humanized_mouse_model_psoriasis-Pharma19B1.pdf' located at http://www.tno.nl/downloads/): (a) Select patients and obtain Medical Ethical Committee approval, (b) Patient donate biopsies, based on informed consent, (c) Biopsies are transplanted onto immune-deficient mice, (d) Peripheral blood mononucleated cells (PBMC) are isolated from patients, (e) The autologous activated PBMC are injected into the xenograft to induce psoriasis, (f) Treatment with investigational drug and determining the inhibition of epidermal (acanthosis) by the anti-IL-23 drug in this humanized mouse model. The results are then compared to a topical treatment with 0.05% betamethasone. This study takes about 7 weeks from the transplantation of the skin to the end of the in vivo treatment.

Also envisaged herein is the use of the polypeptides directed against IL-23 for diagnostic application. The polypeptides herein can be used in methods for determining aberrant expression and/or functioning of IL-23. In particular embodiments this can be in the context of the diagnosis of a specific disease or disorder such as but not limited to disorders of the immune system and immune-mediated inflammatory disorders such as psioriasis, bowel diseases (colitis, Crohn's disease, IBD), infectious diseases, and other autoimmune diseases (such as rheumatoid arthritis, Multiple Sclerosis, Spondyloarthritis, Sarcoidosis, Lupus, Behcet's disease), transplant rejection, cystic fibrosis, asthma, chronic obstructive pulmonary disease, cancer, viral infection, common variable immunodeficiency.

In particular embodiments, methods are envisaged for determining the suitability of a particular treatment of a patient suffering from a disease or disorder such as, but not limited to diseases and disorders listed above.

The application also envisages the use of the polypeptides described herein in methods of screening compositions suitable for the treatment of diseases or disorders such as those described above.

Thus, also envisaged herein are kits comprising the polypeptides envisaged herein for use in a diagnostic or a screening method.

[Parts/Fragments/Analogs/Derivatives]

The application also envisages parts, fragments, analogs, mutants, variants, and/or derivatives of the polypeptides described herein comprising or essentially consisting of one or more of such parts, fragments, analogs, mutants, variants, and/or derivatives, as long as these parts, fragments, analogs, mutants, variants, and/or derivatives are suitable for the prophylactic, therapeutic and/or diagnostic purposes envisaged herein.

Such parts, fragments, analogs, mutants, variants, and/or derivatives are still capable of specifically binding to IL-23.

[Nucleic Acid Sequences]

Also provided herein are nucleic acid sequences encoding single-chain Alphabodies or Alphabody polypeptides, which are obtainable by the methods according to the invention (also referred to herein as 'nucleic acid sequences of the invention') as well as vectors and host cells comprising such nucleic acid sequences.

In a further aspect, the present invention provides nucleic acid sequences encoding the Alphabodies or the polypeptides of the invention (or suitable fragments thereof). These nucleic acid sequences are also referred to herein as nucleic acid sequences of the invention and can also be in the form of a vector or a genetic construct or polynucleotide. The nucleic acid sequences of the invention may be synthetic or semi-synthetic sequences, nucleotide sequences that have been isolated from a library (and in particular, an expression library), nucleotide sequences that have been prepared by PCR using overlapping primers, or nucleotide sequences that have been prepared using techniques for DNA synthesis known per se.

The genetic constructs of the invention may be DNA or RNA, and are preferably double-stranded DNA. The genetic constructs of the invention may also be in a form suitable for transformation of the intended host cell or host organism in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e., a vector that can provide for expression in vitro and/or in vivo (e.g. in a suitable host cell, host organism and/or expression system). The genetic constructs of the invention may comprise a suitable leader sequence to direct the expressed Alphabody to an intended intracellular or extracellular compartment. For example, the genetic constructs of the invention may be inserted in a suitable vector at a pelB leader sequence site to direct the expressed Alphabody to the bacterial periplasmic space. Also the vector may be equipped with a suitable promoter system to, for example, optimize the yield of the Alphabody.

The application also provides vectors and host cells comprising nucleic acids described above. Suitable examples of hosts or host cells for expression of the Alphabodies or polypeptides of the invention will be clear to the skilled person and include any suitable eukaryotic or prokaryotic cell (e.g., bacterial cells such as E. coli, yeast cells, mammalian cells, avian cells, amphibian cells, plant cells, fish cells, and insect cells), whether located in vitro or in vivo.

[Production]

The production of the polypeptides envisaged herein may comprise the step of expressing a nucleotide sequence encoding said polypeptide in a host organism under suitable conditions, so as to produce said polypeptide. This step can be performed by methods known to the person skilled in the art. As known by someone skilled in the art of protein expression and purification, a polypeptide produced from an expression vector using a suitable expression system may be tagged (typically at the N-terminal or C-terminal end of the Alphabody) with e.g. a Histidine or other sequence tag for easy purification.

In addition, the obtained polypeptide sequences having detectable binding affinity for, or detectable in vitro activity on, IL-23, may be synthesized as soluble protein construct.

The invention will now be further described by means of the following non-limiting Examples and Figures, in which the FIGURES show:

FIG. 1. Exemplary sequences of anti-IL-23 polypeptides as envisaged herein; 1: MB23, 2:MA12, 3:MB64, 4:MA5, 5:MA15, 6:MB9, 7:MA9, 8:MB38, 9:MB74, 10:MB67, 11:MA14, 12:MA23, 13:MB43, 14:MB76, 15:MAcons, 16:MBcons, 17:CI59, 18:CI59m, 19:59m_C2eQ; 20:59m_A3cA_A4cS_C2eQ.

FIG. 2. Sequence alignment of Anti-IL-23 polypeptides. The variable positions within the A-helix and C-helix of the Alphabody structure are indicated by their conventional heptad numbering. For example, position 1b in the A-helix corresponds to b-position of the 1st heptad in the A-helix. L1 denotes linker 1 (between the A- and B-helix) and L2 denotes linker 2 (between the B- and C-helix). Linkers marked as 'L8' and 'L16' are respectively 8 and 16 residues in length. The column labeled 'Bhel' shows whether or not position 2f is mutated into Cys (marked as 'B2fC' for B-helix, 2nd heptad, f-position, Cysteine). Amino acids present at the variable positions are listed using single-letter notation. CI59 is the non-matured construct that served as the 'input' sequence for the maturation library.

FIG. 3. Binding parameters of maturation constructs. Polypeptides are the same as in FIGS. 1 and 2. The first data column, labeled 'Eq. ELI. KD', lists the KD values obtained from an equilibrium ELISA assay. The column labeled 'Kin. ELI. KD' shows the KD values obtained from a kinetic ELISA assay. The two preceding columns show the on- and off-rate constants ('Kin. ELI. k_on' and 'Kin. ELI. k_off', respectively) obtained from the same kinetic ELISA experiments. The last column, labeled 'Ph.coat KD', shows the KD values obtained from a phage-coated ELISA assay. 'ND' means not 'determined'.

FIG. 4. Functional parameters of maturation constructs. The column labeled 'Spleno fKD' lists the functional KD values obtained from the mouse splenocyte assay. 'Spleno n data' gives the number of independent repeat experiments. The column labeled 'DB fKD' lists the functional KD values obtained from the DB assay. 'DB n data' is again the number of independent repeats. Only the best performing variants in the splenocyte assay, plus the in silico matured variant CI59m (for which no affinity was determined), were tested in the DB assay.

FIG. 5. Splenocyte IL-17 responses upon stimulation with IL-23. Experiments were conducted in duplicate on cells (500,000) from two different mouse spleens. The indicated concentrations of IL23 (in picoM) were incubated for 72 hours. The dashed line is drawn at 2.6 pM IL-23, which is the concentration that is applied in the standard protocol of the splenocyte assay.

Figure 6:
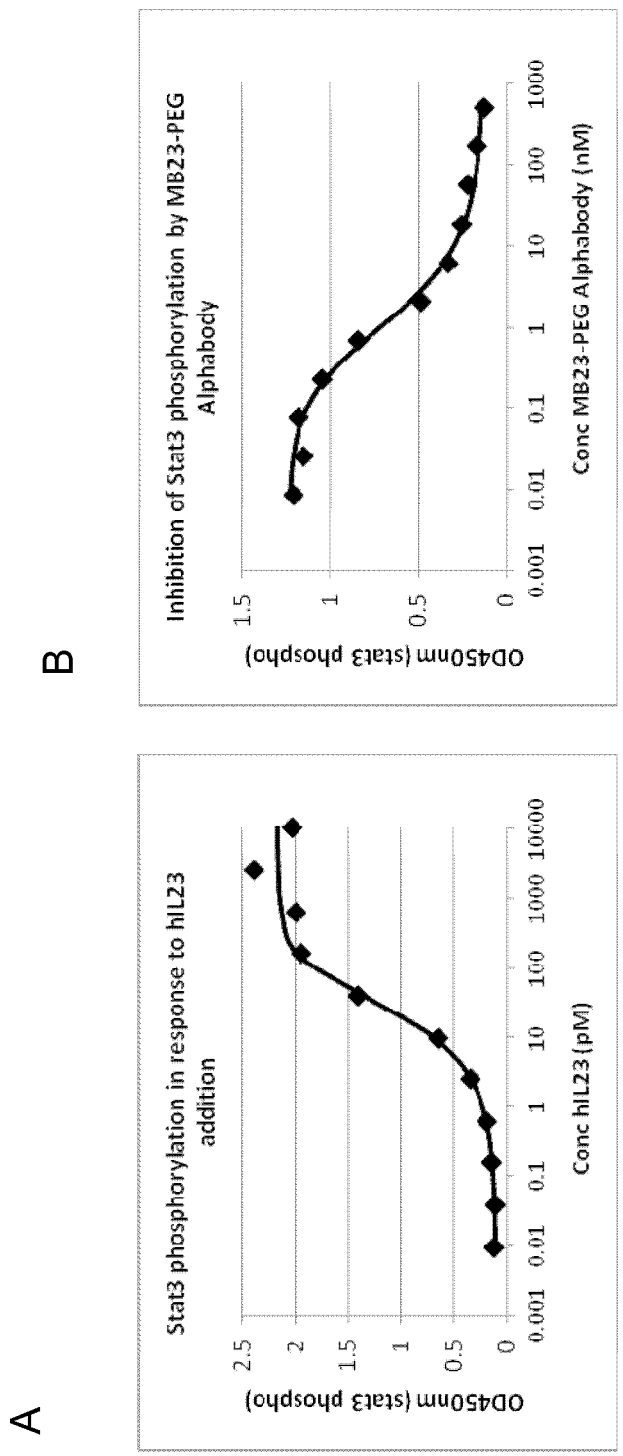

FIG. 6. Human IL23 inhibition by MB23-PEG in the DB cell assay. FIG. 6A shows a representative calibration curve for Stat3 phosphorylation in DB cells upon addition of a concentration range of human IL23 (hIL23). FIG. 6B shows the simultaneously measured inhibition curve of 35 pM hIL23, incubated for 1 hour with a concentration range of MB23-PEG before addition to the DB cells.

Figure 7:
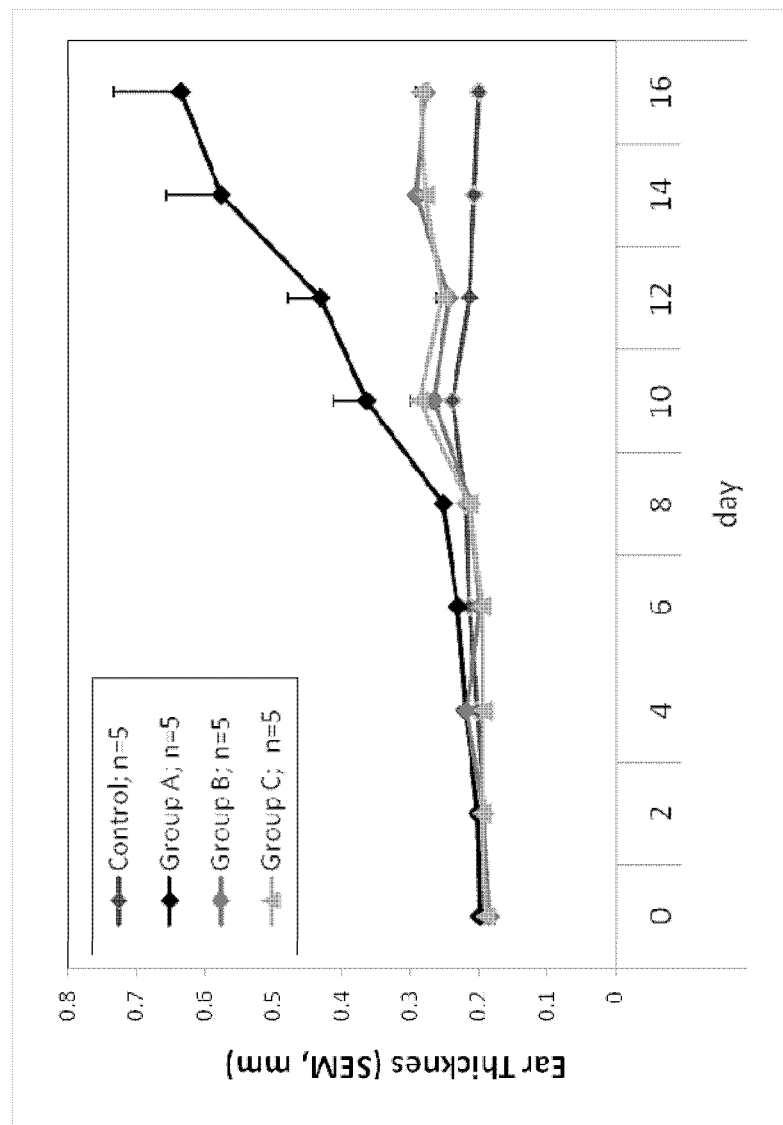

FIG. 7. In vivo prevention of local IL23-induced inflammation in mice. The ear thickness of 20 mice, subdivided into four groups, was measured as a function of time. Control, control group injected with PBS on days 1 to 15 every other day; Groups A-C, mice injected with human IL-23 according to the same scheme; Groups B-C, mice injected also with MB23-PEG on days −1, 0, 3, 6, 9, 12 and 15; Group B, 10 µg intradermal injections; Group C, 40 mg/kg intraperitoneal injections.

EXAMPLES

Production of Polypeptides Specifically Binding to the p19 Subunit of IL-23

1. Production of Look/Peptide Libraries

In one library (referred to as 'scLib_AC11' residues in the A- and C-helices were randomized. The AC11 library comprised Alphabodies with 11 variegated residue positions within the A- and C-helices, the majority of these positions being located at heptad c- and g-positions in the A-helix and at b- and e-positions in the C-helix.

The AC11 library comprised polypeptides comprising Alphabodies with 9 variable residue positions in the groove formed by the A- and C-helices In this library, the L1 and L2 linkers comprise 16-residue Gly/Ser sequences.

These libraries were ordered from GeneArt AG (Germany) and delivered as transformed E. coli cells (strain ER2738, supE strain). The production of phage libraries was further performed as described in WO2010/066740.

2. Biopanning of Polypeptide Libraries Against IL-23

The capturing of the target IL-23 after incubation with the phage library was performed using a biotinylated anti-p40 IL-23 antibody (Biolegend, 508802; clone C8.6) recognizing the subunit p40 of the cytokine IL-23. Prior to incubation with the library, the cytokine IL-23 (eBioscience, 34-8239-85, lot E034049) was incubated with the anti-p40 antibody. This strategy was developed to drive the selections towards binders of the p19 subunit of IL-23 by (partially) blocking the p40 subunit with an antibody. This particular antibody was then also used to immobilize IL-23 on solid support for washing purposes.

Concretely, variable concentrations of IL-23 were incubated at twice the concentration of biotinylated anti-IL-23 p40 antibody in 2% skimmed milk. Five rounds were performed using 200, 200, 100, 10 and 1 nM of IL-23, respectively. In contrast, the concentration of input phage, i.e. phage added to the target in each selection round, remained constant and corresponded to 1E12 phage. Table 1 shows the phagemid output and input as well as the mock (the same biopanning experiment but in absence of target) the output of the different rounds. Selection stringency was increased from R3 on. A high out/mock ratio is seen in R3 and R4.

TABLE 1

Stringency and phagemid input, output in the 5 successive biopanning rounds against hIL-23. The output of the mock biopanning is also shown.

| Round | Target in nM | in | out | mock |
|---|---|---|---|---|
| R1 | 200 | $3\ 10^{12}$ | $4.10^{7}$ | $1 \cdot 10^{6}$ |
| R2 | 200 | $3\ 10^{12}$ | $1.10^{8}$ | $3 \cdot 10^{6}$ |
| R3 | 100 | $3\ 10^{12}$ | $4\ 10^{9}$ | $3\ 10^{6}$ |
| R4 | 10 | $3\ 10^{12}$ | $5\ 10^{9}$ | $1\ 10^{6}$ |
| R5 | 1 | $3\ 10^{12}$ | $2\ 10^{8}$ | $3\ 10^{6}$ |

Dynabeads were added. The beads were then washed 10 times with 1 ml of PBS containing 0.1% of Tween 20 to eliminate non-specific phage. Elution was performed with 200 l of pH2 buffer (100 mM glycine HCl) and neutralized by adding 50 ml of 1M Tris pH8.

A sample of neutralized phagemid solution was added to 1.75 ml of LB. After taking out 50 ml (−1 dilution) for further titration, the rest of the phagemid solution was added to 18 ml of E. coli TG1 cells grown to mid-log phase (OD600 nm=0.5). After a 30 min incubation at 37° C., the solution was centrifuged and the pellet was resuspended in 250 ml of LB+Ampicillin+glucose. Overnight incubation was performed at 37° C. (180 rpm).

The infection culture was plated out on a big 2×TY-AG agar plate.

80 colonies with OD450>0.3 were selected and checked on IL-12 and anti-IL-23p40 antibody coated plates. Positive signals on IL-12 would mean that the Alphabody is recognizing the p40 subunit of IL-23. It was seen that some positive were found to react also with anti-p40 and IL-12.

The best found clones (positive for hIL-23 and negative for IL-12) obtained from these initial biopanning experiments were sequenced. A further selection of the best 11 clones from the AC11 library was then tested in ELISA on their capacity to bind hIL-23 in the absence or presence of neutralizing Ab (NAb) IgG1 Clone B-Z23, directed against the p19 domain. It was found that four of the AC11-derived clones were fully blocked by it.

Since these Alphabodies most likely bind to an epitope on IL-23(p19) overlapping with that of the Nab, these were tested for their ability to neutralize IL-23 (see below).

3. Affinity of Polypeptides to IL-23

To determine the Kd (dissociation constant) for binding to IL-23, the soluble polypeptides were subjected to a (kinetic) Biacore analysis or to Friguet (indirect ELISA) analysis (Friguet et al., 1985, J. Immunol. Methods 77:305-319).

Different clones were identified having binding affinity to IL-23. Clone 59, further referred to as 'Cl59', was found to have a reasonable affinity for human IL-23 (KD=3.8 nM in equilibrium ELISA and 7.0 nM in kinetic ELISA).

4. Identification of a Neutralizing Polypeptide

The biological activity was measured by the well known mouse splenocyte assay in which the production of mouse IL-17 in presence of a predefined concentration of human IL-23 (R&D systems) and in function of a dose-range of IL-23 inhibitory test compound is determined. Alphabodies were pre-incubated at different concentrations (in the range 1.7 nM to 7.1 μM) with a fixed concentration of hIL-23 (typically 2.6 pM). Experiments were done in octuplicate. Also a dilution series of IL-23 without inhibitor (10 pM-0.01 pM) was assayed in quadruplicate as calibration curve to measure the mIL-17 production (Quantikine, mIL-17 kit, R&D systems) in function of the IL-23 concentration. After pre-incubation, mouse splenocytes in medium containing 25 ng/ml mouse IL-2 (R&D systems) were added. As controls Stelara and the IL-23(p19) neutralizing mouse antibody BZ-23 was used.

A recombinant soluble form of clone 59 (SEQ ID NO. 3) was shown to inhibit IL-17 production with a moderate functional KD (fKD=69 nM) in this assay.

5. Optimization by Rational Design Techniques

The Cl59 Polypeptide was further optimized by rational design techniques and the construct named 'Cl59m' (SEQ ID NO: 20) was shown to have an >10-fold improved affinity (ELISA KD=0.3 nM) and a ~5-fold functional improvement in the splenocyte assay (fKD=10-15 nM).

6. Maturation Campaigns

In parallel, two maturation campaigns were performed using a rationally designed 'dedicated library'. These resulted in a large panel of variants with improved affinities. From this panel, 14 variants were selected for further systematic characterization. In addition, two consensus sequences (one from each maturation campaign: MAcons and MBcons, respectively) and three design variants (CI59m (SEQ ID NO: 20), 59m_C2eQ (SEQ ID NO: 21) and 59m_A3cA_A4cS_C2eQ (SEQ ID NO: 22)) were included in the characterization study. FIG. 2 shows the comparison of the variants in terms of variable residues, linker lengths and B-helix modification. It is seen that certain sequences are more hydrophobic than others.

7. Characterization of a Selected Panel of MB23 Alphabodies 7.1 Binding Characteristics FIG. 3 shows various binding data for the 20 studied polypeptides. Except for the last column, all data were obtained for polypeptides expressed in soluble form; the values at the right are for maturation clones still displayed on phage, as fusion constructs to pIII.

It was found that the vast majority of maturation clones (#1-14) nicely fulfilled the expectations and showed sub-nanomolar affinity (with MA14 and MB76 as the exceptions). The highest affinity in standard equilibrium ELISA was measured for MA2 and MA5 (KD=0.1 nM), which is a factor 38 better than the non-matured variant Cl59. Kinetic and equilibrium ELISA data were globally in good agreement, as inferred from the consistence between sub- and supra-nanomolar affinities. A surprising finding was the fact that the main improvement in affinities seemed to have come from an improvement in the on-rates of the matured variants. The correlation coefficient R2 between just the on-rate constants and the KD values themselves was 0.92; indeed, whereas supra-nanomolar binders typically have on-rate constants kon in the order of 105 M-1s-1, the strongest subnanomolar binders have kon values close to or even exceeding 106 M-1s-1.

The phage-coated ELISA KDs were also in pretty good agreement with the KDs obtained for the soluble constructs (with the exception of MB76). This means that KD values measured in the early phase of phage display (i.e., in the screening phase of clones) are quite good predictors of the affinities of soluble constructs.

7.2. Inhibition Data

The inhibitory potencies of soluble Alphabodies were measured routinely in the splenocyte assay described above. A subselection of the most promising variants was subsequently tested in the more laborious DB assay. FIG. 4 shows their potencies and the number of times each Polypeptide was independently tested.

FIG. 5 shows the response curve for IL-17 production by splenocyte cells upon stimulation with IL-23. It was found that the response followed a linear curve as a function of the logarithm of the IL-23 concentration, i.e., the IL-17 response was logarithmic over a very large range of IL-23 concentrations.

The IL-17 production was quantified by a Quantikine kit. A logarithmic relationship between the IL-17 signal (OD) and IL-23 concentration (x-axis) was found.

8. MB23-PEG Production

A two-step chromatography process was developed under reducing conditions (to ensure the single free thiol group on MB23 required for conjugating to the activated maleimide PEG did not lead to dimerization or binding to host cell proteins) resulting in >95% of total protein to be monomeric MB23.

Prior to PEGylation, pooled HIC fractions were concentrated to approximately 5 mg/mL and buffer exchanged into 50 mM MES, 0.5M sodium chloride, pH 6.0 without DTT. Based on the concentration, the moles of product were calculated, and the number of grams of PEG required to equal a 1.5 molar ratio of 40 kDa activated PEG to 10 kDa MB23 protein was determined. Preweighed, solid, activated PEG was mixed directly to the protein solution and the PEG reaction was allowed to proceed overnight at room temperature. After completion of the PEGylation reaction, the PEGylation efficiency was measured by SEC. PEGylated protein was separated from non-PEGylated protein by size exclusion chromatography and the relative percentages of the two species were quantified.

9. Homoconcatemers of the Polypeptide MB23

It was checked whether an increased potency enhancement could be attained by generating a homoconcatemers (aiming at two linked Alphabodies each binding a distinct p19 domain with each p40 domain being bound to a distinct IL12RB1 receptor). Concretely, the MB23_B2fS variant was homoconcatenated via a long 48-residue Gly/Ser linker (construct named MB23_B2fS_L48_MB23_B2fS) and its potency was compared to the non-concatenated form. A second homoconcatemer of a mutant form was also produced (named MB23_B2fK_L48_MB23_B2fK).

The fKDs determined by the splenocyte assay were as follows: (i) MB23_B2fS: 0.55 nM, (ii) MB23_B2fS_L48_MB23_B2fS: 0.14 nM, MB23_B2fK_L48_MB23_B2fK: 0.06 nM. It was concluded that homoconcatenation could result in increased potency 10. In Vitro Efficacy of Anti-IL23 Alphabodies in Human Lymphoma Cells It was found that when increasing concentrations of the PEGylated IL23-specific Alphabody MB23-PEG (produced as described in Example 8) were pre-incubated with a fixed concentration of human IL23, a dose-dependent inhibition of Stat3 phosphorylation was measured (PathScan Phospho-Stat3 Sandwich ELISA kit). In particular, pre-incubation of human IL23 (35 pM) with MB23-PEG (0.01 nM to 500 nM) led to a dose-dependent inhibition of Stat3 phosphorylation, as shown in FIG. 6B. Based on a simultaneously measured calibration curve shown in FIG. 6A, where the Stat3 phosphorylation was measured as a function of the human IL23 concentration (0.01 to 10000 pM), a functional KD of 0.42 nM could be calculated. In a separate experiment, and in the same Stat3 phosphorylation assay, the functional KD for non-PEGylated MB23 Alphabody was determined to be 0.31 nM (data not shown). These results indicate that both PEGylated and non-PEGylated MB23 Alphabodies are able to inhibit human IL23 with about the same potencies.

11. Prevention of Local IL23-Induced Inflammation

Local ear skin inflammation was induced by repeated intradermal administrations of human IL-23 (1 µg) into the right ear pinna of 20 mice (Groups: Control, A, B and C) on days 1 to 15 every other day. The control group (Control) received PBS. MB23-PEG was administered by intradermal (10 µg; Group B) or intraperitoneal (40 mg/kg; Group C) administrations on days −1, 0, 3, 6, 9, 12 and 15. Group A mice did not receive MB23-PEG treatment. Skin swelling was measured by determining the ear skin thickness with a caliper on day 0 and subsequently every other day until day 16. The results are shown in FIG. 7. While the control group did not show any thickening of the ear skin, a clear thickening of the skin was observed as of day 10 for mice that were injected with IL-23 only (group A). In contrast, mice that were also treated with MB23-PEG (groups B and C) did not show significant skin thickening. This indicates that the treatment by MB23-PEG can inhibit the inflammatory effect of human IL-23.

The invention claimed is:

1. An isolated Alphabody polypeptide capable of specifically binding to interleukin-23 (IL-23) comprising an amino acid sequence having the general formula HRS1-L1-HRS2-L2-HRS3,
wherein each of HRS1, HRS2 and HRS3 is independently a heptad repeat sequence (HRS) comprising 2 to 7 consecutive but not necessarily identical heptad repeat units,
wherein said heptad repeat units are 7-residue (poly) peptide fragments represented as 'abcdefg' or 'defgabc', wherein the symbols 'a' to 'g' denote conventional heptad positions and wherein said heptad repeat sequence is represented by (abcdefg)n or (defgabc)n wherein n is between 2 and 7,
wherein at least 50% of all heptad a- and d-positions are occupied by isoleucine residues,
wherein each HRS starts with an aliphatic or aromatic amino acid residue located at a heptad a-position or 'd" position,
wherein each of L1 and L2 are independently a linker fragment, which covalently connect HRS1 to HRS2 and HRS2 to HRS3, respectively,
characterized in that
in HRS1:
(i) the heptad f-position of the second heptad repeat unit is occupied by glutamic acid or alanine,
(ii) the heptad g-position of the second heptad repeat unit is occupied by valine,
(iii) the heptad c-position of the third heptad repeat unit is occupied by alanine or glycine, and
(iv) the heptad g-position of the third heptad repeat unit is occupied by tyrosine or tryptophan, and
in HRS3:
(i) the heptad e-position of the second heptad repeat unit is occupied by glutamine or lysine,
(ii) the heptad b-position of the third heptad repeat unit is occupied by leucine or isoleucine or valine,
(iii) the heptad e-position of the third heptad repeat unit is occupied by tyrosine, and
(iv) HRS3 comprises a partial (a-f) heptad repeat unit following the third heptad repeat and the heptad b-position therein is occupied by methionine.

2. The polypeptide according to claim 1, wherein in HRS1:
(i) the heptad f-position of the second heptad repeat unit is occupied by glutamic acid, and/or
(iii) the heptad c-position of the third heptad repeat unit is occupied by alanine, and/or
(iv) the heptad g-position of the third heptad repeat unit is occupied by tyrosine.

3. The polypeptide according to claim 1, wherein in HRS3:
(i) the heptad e-position of the second heptad repeat unit is occupied by glutamine, and/or
(ii) the heptad b-position of the third heptad repeat unit is occupied by valine.

4. The polypeptide according to claim 1, which is further characterized in that in HRS1:
(i) the heptad b-position of the first heptad repeat unit is occupied by glutamic acid, and/or (ii) the heptad c-position of the first heptad repeat unit is occupied by glutamine, and/or
(iii) the heptad f-position of the first heptad repeat unit is occupied by lysine, and/or
(iv) the heptad g-position of the first heptad repeat unit is occupied by glutamic acid, and/or
(v) the heptad b-position of the second heptad repeat unit is occupied by threonine, and/or
(vi) the heptad c-position of the second heptad repeat unit is occupied by threonine, and/or
(vii) HRS1 comprises a partial (a-c) heptad repeat unit following the third heptad repeat and the c-position therein is occupied by threonine.

5. The polypeptide according to claim 1, which is further characterized in that in HRS3:
(i) the heptad b-position of the second heptad repeat unit is occupied by alanine, and/or
(ii) the heptad f-position of the second heptad repeat unit is occupied by glutamic acid, and/or
(iii) the heptad e-position of the fourth heptad repeat unit is occupied by alanine, and/or
(iv) the heptad f-position of the partial (a-f) heptad repeat unit following the third heptad repeat unit is occupied by serine.

6. The polypeptide according to claim 1, wherein HRS1 has an amino acid sequence as defined in SEQ ID NO: 1 and/or the HRS3 has an amino acid sequence as defined in SEQ ID NO: 2.

7. The polypeptide according to claim 1, wherein said amino acid sequence is as defined in SEQ ID NO: 3.

8. A nucleic acid sequence encoding the polypeptide as defined in claim 1.

9. A pharmaceutical composition comprising a polypeptide according to claim 1 and a pharmaceutically acceptable carrier.

10. A method for the treatment of an IL-23-mediated disease chosen from the group consisting of: inflammation, an inflammatory disorder, infectious diseases, psoriasis, cancer, an autoimmune disease, carcoidis, transplant rejection, cystic fibrosis, asthma, chronic obstructive pulmonary disease, rheumatoid arthritis, viral infection and common variable immunodeficiency, which comprises administering the polypeptide according to claim 1 to a patient in need thereof.

11. The method of claim 10, wherein the inflammatory disorder is a bowel disease.

12. The method of claim 11, wherein the bowel disease is colitis, Crohn's disease, or Inflammatory bowel disease (IBD).

13. The method of claim 10, wherein the autoimmune disease is multiple sclerosis (MS).

* * * * *

SEQUENCE LISTING

<160> NUMBER OF SEQ ID NOS: 28

<210> SEQ ID NO 1
<211> LENGTH: 25
<212> TYPE: PRT
<213> ORGANISM: Artificial
<220> FEATURE:
<223> OTHER INFORMATION: HSR1 of MB23

<400> SEQUENCE: 1

Ile Glu Gln Ile Gln Lys Glu Ile Thr Thr Ile Gln Glu Val Ile Ala
1               5                   10                  15

Ala Ile Gln Lys Tyr Ile Tyr Thr Met

```
                    20                  25

<210> SEQ ID NO 2
<211> LENGTH: 25
<212> TYPE: PRT
<213> ORGANISM: Artificial
<220> FEATURE:
<223> OTHER INFORMATION: HSR3 of MB23

<400> SEQUENCE: 2

Ile Glu Glu Ile Gln Lys Gln Ile Ala Ala Ile Gln Glu Gln Ile Val
1               5                   10                  15

Ala Ile Tyr Lys Gln Ile Met Ala Met
            20                  25

<210> SEQ ID NO 3
<211> LENGTH: 101
<212> TYPE: PRT
<213> ORGANISM: Artificial
<220> FEATURE:
<223> OTHER INFORMATION: Sequence of MB23 Polypeptide

<400> SEQUENCE: 3

Met Ser Ile Glu Gln Ile Gln Lys Glu Ile Thr Thr Ile Gln Glu Val
1               5                   10                  15

Ile Ala Ala Ile Gln Lys Tyr Ile Tyr Thr Met Thr Gly Gly Ser Gly
            20                  25                  30

Gly Ser Gly Gly Met Ser Ile Glu Glu Ile Gln Lys Gln Ile Ala Ala
        35                  40                  45

Ile Gln Cys Gln Ile Ala Ala Ile Gln Lys Gln Ile Tyr Ala Met Thr
    50                  55                  60

Gly Ser Gly Gly Gly Gly Ser Gly Met Ser Ile Glu Glu Ile Gln Lys
65                  70                  75                  80

Gln Ile Ala Ala Ile Gln Glu Gln Ile Val Ala Ile Tyr Lys Gln Ile
                85                  90                  95

Met Ala Met Ala Ser
            100

<210> SEQ ID NO 4
<211> LENGTH: 117
<212> TYPE: PRT
<213> ORGANISM: Artificial
<220> FEATURE:
<223> OTHER INFORMATION: Sequence of MA12 Polypeptide

<400> SEQUENCE: 4

Met Ser Ile Gln Glu Ile Gln Lys Glu Ile Ala Gln Ile Gln Ala Val
1               5                   10                  15

Ile Ala Gly Ile Gln Lys Tyr Ile Tyr Thr Met Thr Gly Gly Ser Gly
            20                  25                  30

Gly Ser Gly Gly Gly Gly Ser Gly Ser Gly Gly Met Ser Ile Glu
        35                  40                  45

Glu Ile Gln Lys Gln Ile Ala Ala Ile Gln Cys Gln Ile Ala Ala Ile
    50                  55                  60

Gln Lys Gln Ile Tyr Ala Met Thr Gly Ser Gly Gly Gly Gly Ser Gly
65                  70                  75                  80

Gly Ser Gly Gly Gly Gly Ser Gly Met Ser Ile Glu Glu Ile Gln Lys
                85                  90                  95

Gln Ile Ala Ala Ile Gln Glu Gln Ile Leu Ala Ile Tyr Lys Gln Ile
                100                 105                 110
```

```
Met Ala Met Val Thr
        115

<210> SEQ ID NO 5
<211> LENGTH: 109
<212> TYPE: PRT
<213> ORGANISM: Artificial
<220> FEATURE:
<223> OTHER INFORMATION: Sequence of MB64 Polypeptide

<400> SEQUENCE: 5

Met Ser Ile Gln Gln Ile Gln Lys Glu Ile Thr Gln Ile Gln Ala Val
1               5                   10                  15

Ile Ala Gly Ile Gln Lys Tyr Ile Tyr Arg Met Thr Gly Gly Ser Gly
            20                  25                  30

Gly Ser Gly Gly Gly Gly Ser Gly Gly Ser Gly Gly Met Ser Ile Glu
        35                  40                  45

Glu Ile Gln Lys Gln Ile Ala Ala Ile Gln Cys Gln Ile Ala Ala Ile
    50                  55                  60

Gln Lys Gln Ile Tyr Ala Met Thr Gly Ser Gly Gly Gly Gly Ser Gly
65                  70                  75                  80

Met Ser Ile Glu Glu Ile Gln Lys Gln Ile Ala Ala Ile Gln Gly Gln
                85                  90                  95

Ile Val Ala Ile Tyr Lys Gln Ile Met Ala Met Ala Thr
            100                 105

<210> SEQ ID NO 6
<211> LENGTH: 109
<212> TYPE: PRT
<213> ORGANISM: Artificial
<220> FEATURE:
<223> OTHER INFORMATION: Sequence of MA5 Polypeptide

<400> SEQUENCE: 6

Met Ser Ile Lys Gln Ile Gln Lys Glu Ile Ala Gln Ile Gln Glu Val
1               5                   10                  15

Ile Ala Ala Ile Gln Lys Trp Ile Tyr Arg Met Thr Gly Gly Ser Gly
            20                  25                  30

Gly Ser Gly Gly Met Ser Ile Glu Glu Ile Gln Lys Gln Ile Ala Ala
        35                  40                  45

Ile Gln Cys Gln Ile Ala Ala Ile Gln Lys Gln Ile Tyr Ala Met Thr
    50                  55                  60

Gly Ser Gly Gly Gly Gly Ser Gly Gly Ser Gly Gly Gly Gly Ser Gly
65                  70                  75                  80

Met Ser Ile Glu Glu Ile Gln Lys Gln Ile Ala Ala Ile Gln Asp Gln
                85                  90                  95

Ile Val Ala Ile Tyr Lys Gln Ile Met Ala Met Ser Ser
            100                 105

<210> SEQ ID NO 7
<211> LENGTH: 109
<212> TYPE: PRT
<213> ORGANISM: Artificial
<220> FEATURE:
<223> OTHER INFORMATION: Sequence of MA15 Polypeptide

<400> SEQUENCE: 7

Met Ser Ile Gln Glu Ile Gln Lys Glu Ile Ala Asn Ile Gln Ala Val
1               5                   10                  15
```

```
Ile Ala Gly Ile Gln Lys Tyr Ile Tyr Thr Met Thr Gly Ser Gly
            20                  25                  30

Gly Ser Gly Gly Gly Ser Gly Gly Ser Gly Gly Met Ser Ile Glu
        35                  40                  45

Glu Ile Gln Lys Gln Ile Ala Ala Ile Gln Cys Gln Ile Ala Ala Ile
 50                  55                  60

Gln Lys Gln Ile Tyr Ala Met Thr Gly Ser Gly Gly Gly Ser Gly
 65                  70                  75                  80

Met Ser Ile Glu Glu Ile Gln Lys Gln Ile Thr Ala Ile Gln Ala Gln
                85                  90                  95

Ile Ile Ala Ile Tyr Lys Gln Ile Met Ala Met Pro Arg
            100                 105
```

```
<210> SEQ ID NO 8
<211> LENGTH: 109
<212> TYPE: PRT
<213> ORGANISM: Artificial
<220> FEATURE:
<223> OTHER INFORMATION: Sequence of MB9 Polypeptide

<400> SEQUENCE: 8

Met Ser Ile Gln Gln Ile Gln Lys Glu Ile Thr Asn Ile Gln Glu Val
 1               5                  10                  15

Ile Ala Ala Ile Gln Lys Trp Ile Tyr Thr Met Thr Gly Gly Ser Gly
            20                  25                  30

Gly Ser Gly Gly Met Ser Ile Glu Glu Ile Gln Lys Gln Ile Ala Ala
        35                  40                  45

Ile Gln Cys Gln Ile Ala Ala Ile Gln Lys Gln Ile Tyr Ala Met Thr
 50                  55                  60

Gly Ser Gly Gly Gly Ser Gly Gly Ser Gly Gly Gly Gly Ser Gly
 65                  70                  75                  80

Met Ser Ile Glu Glu Ile Gln Lys Gln Ile Ala Ala Ile Gln Asn Gln
                85                  90                  95

Ile Leu Ala Ile Tyr Lys Gln Ile Met Ala Met Gly Ser
            100                 105
```

```
<210> SEQ ID NO 9
<211> LENGTH: 109
<212> TYPE: PRT
<213> ORGANISM: Artificial
<220> FEATURE:
<223> OTHER INFORMATION: Sequence of MA9 Polypeptide

<400> SEQUENCE: 9

Met Ser Ile Gln Gln Ile Gln Lys Glu Ile Thr Thr Ile Gln Ala Val
 1               5                  10                  15

Ile Ala Ala Ile Gln Lys Trp Ile Tyr Thr Met Thr Gly Gly Ser Gly
            20                  25                  30

Gly Ser Gly Gly Gly Gly Ser Gly Gly Ser Gly Gly Met Ser Ile Glu
        35                  40                  45

Glu Ile Gln Lys Gln Ile Ala Ala Ile Gln Cys Gln Ile Ala Ala Ile
 50                  55                  60

Gln Lys Gln Ile Tyr Ala Met Thr Gly Ser Gly Gly Gly Ser Gly
 65                  70                  75                  80

Met Ser Ile Glu Glu Ile Gln Lys Gln Ile Ala Ala Ile Gln Gly Gln
                85                  90                  95

Ile Ile Ala Ile Tyr Lys Gln Ile Met Ala Met Lys Asp
            100                 105
```

```
<210> SEQ ID NO 10
<211> LENGTH: 101
<212> TYPE: PRT
<213> ORGANISM: Artificial
<220> FEATURE:
<223> OTHER INFORMATION: Sequence of MB38 Polypeptide

<400> SEQUENCE: 10

Met Ser Ile Gln Glu Ile Gln Lys Glu Ile Lys Gln Ile Gln Glu Val
1               5                   10                  15

Ile Ala Gly Ile Gln Lys Tyr Ile Tyr Gly Met Thr Gly Gly Ser Gly
            20                  25                  30

Gly Ser Gly Gly Met Ser Ile Glu Glu Ile Gln Lys Gln Ile Ala Ala
        35                  40                  45

Ile Gln Cys Gln Ile Ala Ala Ile Gln Lys Gln Ile Tyr Ala Met Thr
    50                  55                  60

Gly Ser Gly Gly Gly Gly Ser Gly Met Ser Ile Glu Glu Ile Gln Lys
65                  70                  75                  80

Gln Ile Ala Ala Ile Gln Asn Gln Ile Leu Ala Ile Tyr Lys Gln Ile
                85                  90                  95

Met Ala Met Pro Gln
            100

<210> SEQ ID NO 11
<211> LENGTH: 109
<212> TYPE: PRT
<213> ORGANISM: Artificial
<220> FEATURE:
<223> OTHER INFORMATION: Sequence of MB74 Polypeptide

<400> SEQUENCE: 11

Met Ser Ile Gln Gln Ile Gln Lys Glu Ile Ala Thr Ile Gln Glu Val
1               5                   10                  15

Ile Ala Gly Ile Gln Lys Tyr Ile Tyr Arg Met Thr Gly Gly Ser Gly
            20                  25                  30

Gly Ser Gly Gly Gly Gly Ser Gly Gly Ser Gly Gly Met Ser Ile Glu
        35                  40                  45

Glu Ile Gln Lys Gln Ile Ala Ala Ile Gln Cys Gln Ile Ala Ala Ile
    50                  55                  60

Gln Lys Gln Ile Tyr Ala Met Thr Gly Ser Gly Gly Gly Gly Ser Gly
65                  70                  75                  80

Met Ser Ile Glu Glu Ile Gln Lys Gln Ile Ala Ala Ile Gln Gly Gln
                85                  90                  95

Ile Leu Ala Ile Tyr Lys Gln Ile Met Ala Met Ala Ile
            100                 105

<210> SEQ ID NO 12
<211> LENGTH: 109
<212> TYPE: PRT
<213> ORGANISM: Artificial
<220> FEATURE:
<223> OTHER INFORMATION: Sequence of MB67 Polypeptide

<400> SEQUENCE: 12

Met Ser Ile Gln Lys Ile Gln Lys Glu Ile Thr Asn Ile Gln Glu Val
1               5                   10                  15

Ile Ala Ala Ile Gln Lys Tyr Ile Tyr Thr Met Thr Gly Gly Ser Gly
            20                  25                  30
```

Gly Ser Gly Gly Met Ser Ile Glu Glu Ile Gln Lys Gln Ile Ala Ala
            35                  40                  45

Ile Gln Cys Gln Ile Ala Ala Ile Gln Lys Gln Ile Tyr Ala Met Thr
        50                  55                  60

Gly Ser Gly Gly Gly Ser Gly Gly Ser Gly Gly Gly Ser Gly
65                  70                  75                  80

Met Ser Ile Glu Glu Ile Gln Lys Gln Ile Ala Ala Ile Gln Arg Gln
                85                  90                  95

Ile Leu Ala Ile Tyr Lys Gln Ile Met Ala Met Ser Thr
                100                 105

<210> SEQ ID NO 13
<211> LENGTH: 101
<212> TYPE: PRT
<213> ORGANISM: Artificial
<220> FEATURE:
<223> OTHER INFORMATION: Sequence of MA14 Polypeptide

<400> SEQUENCE: 13

Met Ser Ile Glu Gln Ile Gln Thr Glu Ile Ala Ser Ile Gln Glu Val
1               5                   10                  15

Ile Ala Gly Ile Gln Lys Tyr Ile Tyr Ser Met Thr Gly Gly Ser Gly
20 25 30

Gly Ser Gly Gly Met Ser Ile Glu Glu Ile Gln Lys Gln Ile Ala Ala
35 40 45

Ile Gln Cys Gln Ile Ala Ala Ile Gln Lys Gln Ile Tyr Ala Met Thr
50 55 60

Gly Ser Gly Gly Gly Gly Ser Gly Met Ser Ile Glu Glu Ile Gln Lys
65 70 75 80

Gln Ile Ala Ala Ile Gln Asn Gln Ile Val Ala Ile Tyr Lys Gln Ile
85 90 95

Met Ala Met Gly Gly
100

<210> SEQ ID NO 14
<211> LENGTH: 101
<212> TYPE: PRT
<213> ORGANISM: Artificial
<220> FEATURE:
<223> OTHER INFORMATION: Sequence of MA23 Polypeptide

<400> SEQUENCE: 14

Met Ser Ile Gln Gln Ile Gln Lys Glu Ile Ala Asn Ile Gln Glu Val
1 5 10 15

Ile Ala Ala Ile Gln Lys Trp Ile Tyr Leu Met Thr Gly Gly Ser Gly
20 25 30

Gly Ser Gly Gly Met Ser Ile Glu Glu Ile Gln Lys Gln Ile Ala Ala
35 40 45

Ile Gln Cys Gln Ile Ala Ala Ile Gln Lys Gln Ile Tyr Ala Met Thr
50 55 60

Gly Ser Gly Gly Gly Gly Ser Gly Met Ser Ile Glu Glu Ile Gln Lys
65 70 75 80

Gln Ile Ala Ala Ile Gln Glu Gln Ile Val Ala Ile Tyr Lys Gln Ile
85 90 95

Met Ala Met Pro Ser
100

<210> SEQ ID NO 15

<211> LENGTH: 109
<212> TYPE: PRT
<213> ORGANISM: Artificial
<220> FEATURE:
<223> OTHER INFORMATION: Sequence of MB43 Polypeptide

<400> SEQUENCE: 15

Met Ser Ile Glu Glu Ile Gln Lys Glu Ile Lys Asn Ile Gln Glu Val
1               5                   10                  15

Ile Ala Ala Ile Gln Lys Tyr Ile Tyr Thr Met Thr Gly Gly Ser Gly
            20                  25                  30

Gly Ser Gly Gly Met Ser Ile Glu Glu Ile Gln Lys Gln Ile Ala Ala
        35                  40                  45

Ile Gln Cys Gln Ile Ala Ala Ile Gln Lys Gln Ile Tyr Ala Met Thr
50                  55                  60

Gly Ser Gly Gly Gly Ser Gly Gly Ser Gly Gly Gly Ser Gly
65                  70                  75                  80

Met Ser Ile Glu Glu Ile Pro Lys Gln Ile Ala Ala Ile Gln Asp Gln
                85                  90                  95

Ile Ile Ala Ile Tyr Lys Gln Ile Met Ala Met Thr Arg
            100                 105

<210> SEQ ID NO 16
<211> LENGTH: 101
<212> TYPE: PRT
<213> ORGANISM: Artificial
<220> FEATURE:
<223> OTHER INFORMATION: Sequence of MB76 Polypeptide

<400> SEQUENCE: 16

Met Ser Ile Gln Gln Ile Gln Lys Glu Ile Thr Gln Ile Gln Glu Val
1               5                   10                  15

Ile Ala Ala Ile Gln Lys Tyr Ile Tyr Arg Met Thr Gly Gly Ser Gly
            20                  25                  30

Gly Ser Asp Gly Met Ser Ile Glu Glu Ile Gln Lys Gln Ile Ala Ala
        35                  40                  45

Ile Gln Cys Gln Ile Ala Ala Ile Gln Lys Gln Ile Tyr Ala Met Thr
50                  55                  60

Gly Ser Gly Gly Gly Ser Gly Met Ser Ile Glu Glu Ile Gln Lys
65                  70                  75                  80

Gln Ile Ala Ala Ile Gln Gly Gln Ile Leu Ala Ile Tyr Lys Gln Ile
                85                  90                  95

Met Ala Met Ser Leu
            100

<210> SEQ ID NO 17
<211> LENGTH: 109
<212> TYPE: PRT
<213> ORGANISM: Artificial
<220> FEATURE:
<223> OTHER INFORMATION: Sequence of MAcons Polypeptide

<400> SEQUENCE: 17

Met Ser Ile Gln Gln Ile Gln Lys Glu Ile Ala Gln Ile Gln Glu Val
1               5                   10                  15

Ile Ala Ala Ile Gln Lys Trp Ile Tyr Ser Met Thr Gly Gly Ser Gly
            20                  25                  30

Gly Ser Gly Gly Gly Gly Ser Gly Gly Ser Gly Gly Met Ser Ile Glu
        35                  40                  45

```
Glu Ile Gln Lys Gln Ile Ala Ala Ile Gln Cys Gln Ile Ala Ala Ile
    50                  55                  60

Gln Lys Gln Ile Tyr Ala Met Thr Gly Ser Gly Gly Gly Gly Ser Gly
65                  70                  75                  80

Met Ser Ile Glu Glu Ile Gln Lys Gln Ile Ala Ala Ile Gln Asp Gln
                85                  90                  95

Ile Val Ala Ile Tyr Lys Gln Ile Met Ala Met Ser Gly
            100                 105
```

<210> SEQ ID NO 18
<211> LENGTH: 100
<212> TYPE: PRT
<213> ORGANISM: Artificial
<220> FEATURE:
<223> OTHER INFORMATION: Sequence of MBcons Polypeptide

<400> SEQUENCE: 18

```
Met Ser Ile Glu Glu Ile Gln Lys Gln Ile Ala Ser Ile Gln Glu Val
1               5                   10                  15

Ile Ala Gly Ile Gln Lys Trp Ile Tyr Met Met Thr Gly Gly Ser Gly
            20                  25                  30

Gly Ser Gly Gly Met Ser Ile Glu Glu Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Gly Ser Gly Gly Ser Gly Met Ser Ile Glu Glu Ile Gln Lys Gln
65                  70                  75                  80

Ile Thr Ala Ile Lys Glu Gln Ile Ala Ile Tyr Lys Gln Ile Met
                85                  90                  95

Ala Met Thr Pro
            100
```

<210> SEQ ID NO 19
<211> LENGTH: 102
<212> TYPE: PRT
<213> ORGANISM: Artificial
<220> FEATURE:
<223> OTHER INFORMATION: Sequence of C159 Polypeptide

<400> SEQUENCE: 19

```
Met Ser Ile Glu Glu Ile Gln Lys Gln Ile Ala Ser Ile Gln Glu Val
1               5                   10                  15

Ile Ala Gly Ile Gln Lys Trp Ile Tyr Met Met Thr Gly Gly Ser Gly
            20                  25                  30

Gly Ser Gly Gly Met Ser Ile Glu Glu Ile Gln Lys Gln Ile Ala Ala
        35                  40                  45

Ile Gln Lys Gln Ile Ala Ala Ile Gln Lys Gln Ile Tyr Ala Met Thr
    50                  55                  60

Gly Gly Ser Gly Gly Gly Gly Ser Gly Met Ser Ile Glu Glu Ile Gln
65                  70                  75                  80

Lys Gln Ile Thr Ala Ile Lys Glu Gln Ile Ile Ala Ile Tyr Lys Gln
                85                  90                  95

Ile Met Ala Met Thr Pro
            100
```

<210> SEQ ID NO 20
<211> LENGTH: 117
<212> TYPE: PRT
<213> ORGANISM: Artificial

-continued

<220> FEATURE:
<223> OTHER INFORMATION: Sequence of C159m Polypeptide

<400> SEQUENCE: 20

Met Ser Ile Gln Gln Ile Gln Lys Glu Ile Ala Gln Ile Gln Glu Val
1               5                   10                  15

Ile Ala Gly Ile Gln Lys Trp Ile Tyr Met Met Thr Gly Gly Ser Gly
            20                  25                  30

Gly Gly Ser Gly Gly Gly Ser Gly Gly Ser Gly Met Ser Ile Glu
        35                  40                  45

Glu Ile Gln Lys Gln Ile Ala Ala Ile Gln Lys Gln Ile Ala Ala Ile
    50                  55                  60

Gln Lys Gln Ile Tyr Ala Met Thr Gly Gly Ser Gly Gly Gly Ser Gly
65                  70                  75                  80

Gly Gly Ser Gly Gly Gly Ser Gly Met Ser Ile Glu Glu Ile Gln Lys
                85                  90                  95

Gln Ile Thr Ala Ile Lys Glu Gln Ile Ile Ala Ile Tyr Lys Gln Ile
            100                 105                 110

Met Ala Met Thr Pro
        115

<210> SEQ ID NO 21
<211> LENGTH: 117
<212> TYPE: PRT
<213> ORGANISM: Artificial
<220> FEATURE:
<223> OTHER INFORMATION: Sequence of 59m_C2eQ Polypeptide

<400> SEQUENCE: 21

Met Ser Ile Gln Gln Ile Gln Lys Glu Ile Ala Gln Ile Gln Glu Val
1               5                   10                  15

Ile Ala Gly Ile Gln Lys Trp Ile Tyr Met Met Thr Gly Gly Ser Gly
            20                  25                  30

Gly Ser Gly Gly Gly Gly Ser Gly Gly Ser Gly Gly Met Ser Ile Glu
        35                  40                  45

Glu Ile Gln Lys Gln Ile Ala Ala Ile Gln Cys Gln Ile Ala Ala Ile
    50                  55                  60

Gln Lys Gln Ile Tyr Ala Met Thr Gly Ser Gly Gly Gly Ser Gly
65                  70                  75                  80

Gly Ser Gly Gly Gly Gly Ser Gly Met Ser Ile Glu Glu Ile Gln Lys
                85                  90                  95

Gln Ile Thr Ala Ile Gln Glu Gln Ile Ile Ala Ile Tyr Lys Gln Ile
            100                 105                 110

Met Ala Met Thr Pro
        115

<210> SEQ ID NO 22
<211> LENGTH: 117
<212> TYPE: PRT
<213> ORGANISM: Artificial
<220> FEATURE:
<223> OTHER INFORMATION: Sequence of 59m_A3cA_A4cS_C2eQ Polypeptide

<400> SEQUENCE: 22

Met Ser Ile Gln Gln Ile Gln Lys Glu Ile Ala Gln Ile Gln Glu Val
1               5                   10                  15

Ile Ala Ala Ile Gln Lys Trp Ile Tyr Ser Met Thr Gly Gly Ser Gly
            20                  25                  30

-continued

Gly Ser Gly Gly Gly Ser Gly Gly Ser Gly Met Ser Ile Glu
            35                  40                  45

Glu Ile Gln Lys Gln Ile Ala Ala Ile Gln Cys Gln Ile Ala Ala Ile
 50                  55                  60

Gln Lys Gln Ile Tyr Ala Met Thr Gly Ser Gly Gly Gly Ser Gly
 65                  70                  75                  80

Gly Ser Gly Gly Gly Gly Ser Gly Met Ser Ile Glu Glu Ile Gln Lys
            85                  90                  95

Gln Ile Thr Ala Ile Gln Glu Gln Ile Ile Ala Ile Tyr Lys Gln Ile
                100                 105                 110

Met Ala Met Thr Pro
        115

<210> SEQ ID NO 23
<211> LENGTH: 8
<212> TYPE: PRT
<213> ORGANISM: Artificial
<220> FEATURE:
<223> OTHER INFORMATION: Repeat sequence of Linker 1

<400> SEQUENCE: 23

Gly Gly Ser Gly Gly Ser Gly Gly
1               5

<210> SEQ ID NO 24
<211> LENGTH: 8
<212> TYPE: PRT
<213> ORGANISM: Artificial
<220> FEATURE:
<223> OTHER INFORMATION: Repeat sequence of Linker 2

<400> SEQUENCE: 24

Gly Ser Gly Gly Gly Gly Ser Gly
1               5

<210> SEQ ID NO 25
<211> LENGTH: 12
<212> TYPE: PRT
<213> ORGANISM: Artificial
<220> FEATURE:
<223> OTHER INFORMATION: Exemplary linker sequence

<400> SEQUENCE: 25

Met Thr Gly Gly Ser Gly Gly Ser Gly Gly Met Ser
1               5                   10

<210> SEQ ID NO 26
<211> LENGTH: 20
<212> TYPE: PRT
<213> ORGANISM: Artificial
<220> FEATURE:
<223> OTHER INFORMATION: Exemplary linker sequence

<400> SEQUENCE: 26

Met Thr Gly Gly Ser Gly Gly Ser Gly Gly Gly Ser Gly Gly Ser
1               5                   10                  15

Gly Gly Met Ser
        20

<210> SEQ ID NO 27
<211> LENGTH: 24
<212> TYPE: PRT
<213> ORGANISM: Artificial
<220> FEATURE:

```
<223> OTHER INFORMATION: Exemplary sequence HSR2

<400> SEQUENCE: 27

Ile Glu Glu Ile Gln Lys Gln Ile Ala Ala Ile Gln Cys Gln Ile Ala
1               5                   10                  15

Ala Ile Gln Lys Gln Ile Tyr Ala
            20

<210> SEQ ID NO 28
<211> LENGTH: 110
<212> TYPE: PRT
<213> ORGANISM: Artificial Sequence
<220> FEATURE:
<223> OTHER INFORMATION: MB23 phage sequence

<400> SEQUENCE: 28

Met Ser Ile Glu Gln Ile Gln Lys Glu Ile Thr Thr Ile Gln Glu Val
1               5                   10                  15

Ile Ala Ala Ile Gln Lys Tyr Ile Tyr Thr Met Thr Gly Gly Ser Gly
            20                  25                  30

Gly Ser Gly Gly Met Ser Ile Glu Glu Ile Gln Lys Gln Ile Ala Ala
        35                  40                  45

Ile Gln Glu Gln Ile Ala Ala Ile Gln Lys Gln Ile Tyr Ala Met Thr
    50                  55                  60

Gly Ser Gly Gly Gly Ser Gly Met Ser Ile Glu Glu Ile Gln Lys
65                  70                  75                  80

Gln Ile Ala Ala Ile Gln Glu Gln Ile Val Ala Ile Tyr Lys Gln Ile
                85                  90                  95

Met Ala Met Ala Ser Ala Ala Ala His His His His His His
                100                 105                 110
```